(12) United States Patent
D'Onofrio et al.

(10) Patent No.: US 9,550,047 B2
(45) Date of Patent: Jan. 24, 2017

(54) BALLOON CATHETER WITH POLYMERIC BALLOON HAVING A SURFACE MODIFIED BY A PHOTOACTIVATION REACTION AND METHOD OF MAKING

(75) Inventors: Simone D'Onofrio, Brescia (IT); Paolo Pellegrini, Brescia (IT)

(73) Assignee: Invatec S.P.A., Roncadelle (IT)

( * ) Notice: Subject to any disclaimer, the term of this patent is extended or adjusted under 35 U.S.C. 154(b) by 299 days.

(21) Appl. No.: 14/240,320

(22) PCT Filed: Sep. 27, 2011

(86) PCT No.: PCT/EP2011/066788
§ 371 (c)(1),
(2), (4) Date: Mar. 14, 2014

(87) PCT Pub. No.: WO2013/044942
PCT Pub. Date: Apr. 4, 2013

(65) Prior Publication Data
US 2014/0378897 A1 Dec. 25, 2014

(51) Int. Cl.
*B29D 22/00* (2006.01)
*A61M 25/10* (2013.01)
*A61L 29/08* (2006.01)
*A61L 29/14* (2006.01)
*B05D 3/06* (2006.01)

(52) U.S. Cl.
CPC ........... *A61M 25/104* (2013.01); *A61L 29/085* (2013.01); *A61L 29/14* (2013.01); *B05D 3/06* (2013.01); *A61L 2400/18* (2013.01); *A61M 2025/1088* (2013.01); *Y10T 428/1334* (2015.01)

(58) Field of Classification Search
CPC .................. A61M 25/104; A61M 2025/1047; A61M 2025/1088; B05D 3/06; B05D 3/061; A61L 77/00; A61L 77/12; A61L 77/06; G03F 7/008; Y10T 428/1334
USPC .............. 428/35.2; 427/2.1, 2.24; 604/95.03, 604/96.01, 101.04, 103.02, 103.06, 604/103.07, 103.11; 606/192, 194; 528/310, 323; 264/331.19
See application file for complete search history.

(56) References Cited

U.S. PATENT DOCUMENTS

| | | |
|---|---|---|
| 5,061,738 A | 10/1991 | Solomon et al. |
| 5,258,041 A | 11/1993 | Guire et al. |
| 5,415,619 A | 5/1995 | Lee et al. |
| 5,714,360 A | 2/1998 | Swan et al. |
| 5,830,539 A * | 11/1998 | Yan .................. A61L 27/28 427/2.13 |
| 6,120,904 A | 9/2000 | Hostettler et al. |
| 6,506,333 B1 | 1/2003 | Qin et al. |
| 6,551,267 B1 | 4/2003 | Cohen et al. |

FOREIGN PATENT DOCUMENTS

| | | |
|---|---|---|
| WO | WO98/22541 | 5/1998 |
| WO | WO2005/037337 | 4/2005 |
| WO | WO2007/132485 | 11/2007 |

OTHER PUBLICATIONS

PCT/EP2011/066788, Int'l Preliminary Report on Patentability and Written Opinion, mailed Apr. 10, 2014.
(Continued)

*Primary Examiner* — Ruiyun Zhang

(57) ABSTRACT

A balloon catheter, in particular a balloon catheter for angioplasty, the balloon having an inner or outer surface modified by means of a photoactivation reaction.

27 Claims, 13 Drawing Sheets

(56) References Cited

OTHER PUBLICATIONS

Feng Shi et al. "To Adjust Wetting Properties of Organic Surface by in Situ Photoreaction of Aromatic Azide", Langmuri 2007, 23(3), 1253-1257.

A.P. Van der Heiden et al. "Adsorption of Proteins onto Poly(ether urethane) with a Phosphorylcholine Moiety and Influence of Preabsorbed Phospholipid" Journal of Biomedical Materials Research (1998), 40(2), 195-203.

Leonard W. Schwartz et al., "Contact Angle Hysteresis on Heterogeneous Surfaces" Langmuir 1985, 1, pp. 219-230.

Y.L. Chen et al., "Molecular Mechanisms Associated With Adhesion and Contact Angle Hysteresis of Monolayer Surfaces" J. Phys. Chem. 1991, 95, pp. 10736-10747.

J.H. Wang, et al., "Dynamic Contact Angles and Contact Angle Hysteresis of Plasma Polymers" Langmuir 1994, 10, pp. 3887-3871.

Lorraine M. Lander et al., "A Systematic Comparison of Contact Angle Methods" Langmuir, 1993, 9, pp. 2237-2239.

Jia, Xinqiao et al. "Nylon Surface Modification. Part 1. Targeting the Amide Groups for Selective Introduction of Reactive Functionalities" Polymer, 47 (2006), 4916-4924.

G.A. Wiese et al. "Preparation of Tris (hydroxymethyl) Sulfanilamidomethane" Journal of the American Pharmaceutical Association, S.E., vol. 37, Issue 9, 380-383 (1948).

S. Duckett et al. "Foundations of Spectroscopy" Oxford University Press, 2000.

H. Brintzinger et al., "Amid-Und Ester-amid-Bildung Zwischen Carbonsaurechloriden and Mono- , Di-Und Triathanolamin" Chemische Berichte 82, 201 (1949).

M.L. Crossley, et al., "Sulfanilamide Derivatives VI Substituted N-Aliphatic Sulfaniamides" J. Am. Chem. Soc. 62 (3), pp. 532-534 (1940).

S.J. Pastine, et al. "Facile UV Patterning of Robust Carbon Nanotube Forests Using Perfluoroarylazides" Am. Chem. Soc. 2008, 130, 4238-4239.

R.E. Galardy et al, "Photoaffinity Labeling of Peptide Hormore Binding Sites," The Journal of Biological Chemistry, col. 249, No. 11, pp. 2510-2618, 1974.

\* cited by examiner

Fig. 3A

Table 2

| Sample | Material | $\theta_{rec}$ | $\theta_{rec}$ (stdev) | $\theta_{adv}$ | $\theta_{adv}$ (stdev) | $\theta_{hist}$ |
|---|---|---|---|---|---|---|
| S1 | PA12 | 47,70 | 3,418 | 86,09 | 4,601 | 38,39 |
| S2 | TRIS | 29,50 | 5,715 | 71,57 | 4,049 | 42,08 |
| S3 | pnPTFE | 43,78 | 3,942 | 92,25 | 4,032 | 48,47 |
| S4 | pnTRIS | 13,63 | 7,107 | 63,87 | 5,408 | 50,25 |
| S5 | pnPEG | 39,33 | 6,768 | 78,99 | 4,716 | 39,67 |
| S6 | pnALC | 36,34 | 4,904 | 92,16 | 2,557 | 55,82 |

Table 3

| Sample | Material | $\theta_{rec}$ | $\theta_{adv}$ |
|---|---|---|---|
| S2 | TRIS | 38,17% | 16,87% |
| S3 | pnPTFE | 8,23% | -7,15% |
| S4 | pnTRIS | 71,44% | 25,81% |
| S5 | pnPEG | 17,56% | 8,25% |
| S6 | pnALC | 23,83% | -7,04% |

Fig. 6A

Table 5

| Sample | Material | $\theta_{rec}$ | $\theta_{rec}$ (stdev) | $\theta_{adv}$ | $\theta_{adv}$ (stdev) |
|---|---|---|---|---|---|
| S7 | PA12 | 44,45 | 7,050 | 83,16 | 2,354 |
| S8 | pnTRIS | 14,38 | 6,245 | 69,12 | 5,943 |
| S9 | pnALC | 45,98 | 3,920 | 88,35 | 5,461 |

Table 6

| Sample | Material | $\theta_{rec}$ | $\theta_{adv}$ |
|---|---|---|---|
| S8 | pnTRIS | 67,64 | 16,89 |
| S9 | pnALC | -3,44 | -6,24 |

BALLOON CATHETER WITH POLYMERIC BALLOON HAVING A SURFACE MODIFIED BY A PHOTOACTIVATION REACTION AND METHOD OF MAKING

The present invention relates to a balloon catheter for endovascular interventions.

In particular, the present invention relates to a balloon catheter having a balloon surface endowed with improved properties.

More in particular, the present invention relates to a balloon catheter with a balloon surface that is modified through a photoactivation reaction in order to confer suitable properties to at least a portion of the balloon surface.

Nowadays endovascular interventions are widely accepted procedures for treating different types of vascular diseases. For instance, angioplasty is a procedure for opening narrowed or even blocked blood vessels and restoring the normal blood flow. Angioplasty is successfully used also for treating coronary arteries, e.g. for treating coronary stenoses present therein.

For carrying out an endovascular procedure, a catheter (e.g. an angioplasty catheter) is inserted into a blood vessel of the patient (the blood vessel of an arm or of the groin, for instance) and then pushed to the intervention site, e.g. an occluded or partially occluded blood vessel (vein or artery). In order for the catheter to be correctly placed, typically a guide wire is firstly inserted into the blood vessel (optionally in combination with a guiding catheter) for allowing the correct positioning of the endovascular catheter, such as a balloon catheter, a stent delivery system, a clot extraction catheter, or a multipurpose catheter. In case of an angioplasty procedure, the subsequent operations of inflating and deflating the balloon result in stretching and thinning the vessel wall to increase the lumen diameter for re-establishing an acceptable blood flow.

There are continuous efforts in the art in order to improve the characteristics of the medical devices for endovascular procedures. In particular the size, flexibility, pushability and slidability properties of these medical devices are always taken into great consideration and possibly subject to continuous improvements. Moreover, in case a medical device is used which is suitable for delivering a therapeutic agent (e.g. to avoid restenosis due to vessel dilatation and/or stent implantation following an angioplasty procedure), also the efficacy of delivery of the therapeutic agent (e.g. the efficacy of transport of the therapeutic agent along the vascular system as well as the efficacy of the therapeutic agent uptake into the vessel wall at the intervention site) is subject to continuous improvements.

Size is a crucial factor due to the very small dimensions of the vessels the medical devices have to be inserted in, especially when coronary arteries are treated. Small size, in terms of device diameter, is highly desirable in order to avoid damages to the vessel wall.

Flexibility must also be met, so that the medical device may suitably follow the vessel path, especially in case of particularly tortuous vessels.

Pushability refers to the possibility of a medical device to be easily pushed by the physician through the vascular system to the intervention site, while slidability relates to the capability of the medical device to move along the vascular system with reduced friction.

As far as slidability is concerned, it is preferred that a negligible friction exists between the inner surface of the catheter and the outer surface of the guide wire, as well as between the outer surface of the balloon and/or of the catheter shaft and the vessel wall so that the delivery of the balloon catheter within the vascular system can be easily performed by the physician with no relevant efforts and reducing to a minimum the risk of damaging the vessel wall.

In order to reduce the friction and to improve the slidability property of a balloon catheter, the outer surface of the catheter shaft and/or of the catheter balloon is generally provided with a hydrophilic coating that suitably increases the lubricity of the balloon catheter while travelling along the vascular system.

Furthermore, at least two main procedures for the surface modification of polymers are known in the art.

According to a first procedure, the surface of a polymeric material can be modified by acting on its composition and/or microstructure.

According to a second procedure, a coating of a material endowed with the required characteristics is applied onto the polymeric material surface to be modified.

For instance, U.S. Pat. No. 5,714,360 discloses the covalent linkage of a target molecule, selected among synthetic polymers, especially polyvinylpirrolidone, carbohydrates, proteins, lipids, nucleic acids, drugs, dyes and fluorescent compounds, capable of conferring a particular property to a substrate through a photoactivating linking agent. U.S. Pat. No. 6,551,267 discloses a plastic material article coated with a crosslinked hydrogel permanently bound to the inner wall of the tube. U.S. Pat. No. 6,120,904 discloses the formation of a polyurethane/polyurea hydrogel coating onto a plasma treated surface. U.S. Pat. No. 5,415,619 describes the modification of a polyester surface with the reaction of sulphuric acid which originates negative charges; the further treatment with perchloric acid leads to the insertion of hydrophilic functional groups like hydroxyl groups. Polyamide surfaces may also be modified according to the method disclosed in *Polymer* (2006, vol. 47, 14, 4916-4924) with the use of a strong base like potassium terbutylate; the potassium salt thus formed may bind other useful molecules.

The method of applying a coating may be performed by dipping or spraying as taught, for instance, in U.S. Pat. No. 5,061,738 wherein a mixture of a silicone resin and heparin is applied to a tube surface.

Alternatively, extrusion and co-extrusion techniques may be used, wherein a lubricating hydrophilic polymer immiscible with the tube material and the tube material are co-extruded, as disclosed for instance in U.S. Pat. No. 6,506,333.

The article "To adjust wetting properties of organic surface by in situ photoreaction of aromatic azide" published by Feng Shi et al., *Langmuir* 2007, 23(3), 1253-1257, discloses an alkyl or substituted alkyl chain, such as halogen substituted chain, that may impart hydrophobic property to a modified polymeric surface.

The article "Adsorption of proteins onto poly(ether urethane) with a phosphorylcholine moiety and influence of preadsorbed phospholipid" published by A. P. van der Heiden et al., *Journal of Biomedical Materials Research* (1998), 40(2), 195-203, discloses a PEU film that is photochemically modified with a PC-containing aryl azide.

U.S. Pat. No. 5,258,041 discloses a method for attaching a biomolecule to a support having a hydrophobic surface, the method involving the use of a long chain chemical spacer having a hydrophobic guiding group capable of becoming embedded in the surface, and the biomolecule being covalently bound to the spacer at its opposite end.

None of the prior art methods mentioned above is suitable for giving the desired hydrophilic or hydrophobic properties to the balloon surface of a balloon catheter without negatively affecting the other performances thereof.

For instance, generally an applied coating is not very stable and can be removed, damaged or degraded, such as delaminated or peeled, while the catheter is being used.

On the other hand, plasma treatments, which modify the surface of the medical device material, may cause damages to the surface itself and do not provide reproducible results.

The use of chemical reactions for the introduction of functional groups into the polymeric material may lead to structural alterations of the surface and sometimes an insufficient functionalisation is obtained.

Finally, the compounding techniques are complex and difficult to set up in order to obtain reproducible results. Moreover, said techniques are also quite expensive.

Accordingly, the Applicant has perceived the need of providing a reliable and reproducible method which is suitable for modifying the balloon surface of a balloon catheter.

OBJECT OF THE INVENTION

It is an object of the present invention a balloon catheter, the balloon surface of which is modified via a photoactivation reaction by means of substituted aromatic azides.

In particular, said photoactivation reaction imparts either hydrophobic or hydrophilic properties to the balloon surface of the balloon catheter.

Alternatively, said photoactivation reaction can be used to bind any given substance of interest (e.g. a therapeutic agent) to the balloon modified surface.

BRIEF DESCRIPTION OF THE FIGURES

FIG. 3A shows Tables 2 and 3.

FIG. 6A shows Tables 5 and 6.

DETAILED DISCLOSURE OF THE INVENTION

Figure 1:
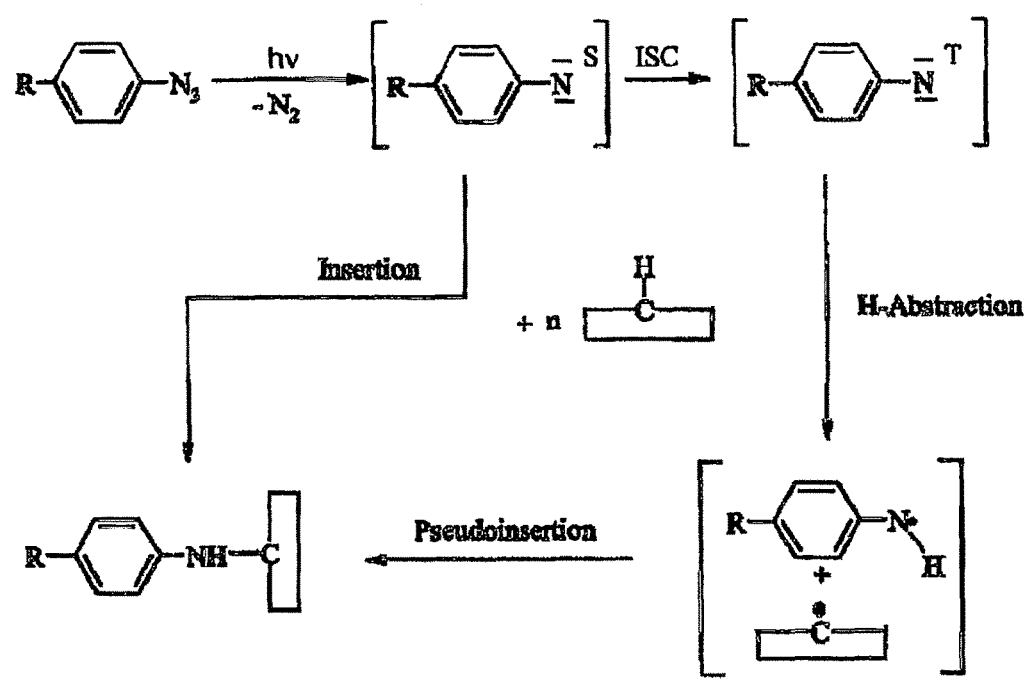
FIG. 1 shows the mechanism of insertion of the para-substituted arylazide compounds of the invention into a C—H containing surface.

According to an embodiment of the present invention a balloon catheter comprises a balloon made of a polymeric material, the outer surface of the balloon being modified through photoactivation reaction by the insertion of hydrophilic moieties.

The hydrophilic outer surface of the balloon modified according to the present invention allows to advantageously decrease the friction coefficient of the balloon outer surface of the balloon catheter so that the latter can be easily moved along the vascular system without damaging the vessel wall.

Alternatively, the hydrophilic outer surface of the balloon modified according to the present invention, can be advantageously used, for instance, to bind a carrier (e.g. a nanoparticle) for transporting a given agent (e.g. a therapeutic or diagnostic agent) to an intervention site.

According to a further embodiment of the present invention a balloon catheter comprises a balloon made of a polymeric material, the inner surface of the balloon being modified through photoactivation reaction by the insertion of hydrophilic moieties.

The hydrophilic inner surface of the balloon modified according to the present invention allows to advantageously decrease the friction coefficient of the balloon inner surface of the balloon catheter. This conferred property can contribute in reducing the balloon inflation and deflation times during an endovascular intervention (e.g. an angioplasty procedure), an aspect which is particularly relevant in case long balloons (having a length of up to 300 mm) are involved (it is apparent that the balloon length sensibly increased the balloon inflation/deflation times).

According to a further embodiment of the present invention a balloon catheter comprises a balloon made of a polymeric material, the outer surface of the balloon being modified through photoactivation reaction by the insertion of hydrophobic moieties.

The hydrophobic outer surface of the balloon modified according to the present invention, can be advantageously used, for instance, to bind a carrier (e.g. a nanoparticle) for transporting a given agent (e.g. a therapeutic or diagnostic agent) to an intervention site.

Alternatively, the balloon hydrophobic outer surface can be advantageously used for improving the capability of the balloon to pass through a vessel occlusion (e.g. a chronic total occlusion). In fact, thanks to the affinity of the hydrophobic surface with the material of the vessel occlusion, the balloon with the modified outer surface can better penetrate and move along a vessel occlusion.

According to a further embodiment of the present invention, a balloon catheter comprises a balloon made of a polymeric material, the inner surface of the balloon being modified through photoactivation reaction by the insertion of hydrophobic moieties.

A possible advantage of this further embodiment is to prevent an undesirable adhesion between polymer layers which may occur during the product shelf life. This is a significant problem since this adhesion (which blocks and sticks the balloon folds) may cause tears and pinhole failures upon the balloon first inflation.

According to a further embodiment, a balloon catheter comprises a drug eluting balloon (i.e. a balloon provided with an active substance, e.g. a therapeutic agent, which can be released at a given intervention site), the outer surface of which is modified through photoactivation reaction according to the present invention so as to suitably bind at least one active substance to at least one portion of the balloon outer surface. The active substance can be directly bound to the modified surface or, alternatively, the active substance can be bound to the modified surface by means of a bridge substance that is suitable for linking or encapsulating the active substance. Suitable active substances are: antiproliferative, antiinflammatory, antiphlogistic, antihyperplastic, antineoplastic, antimitotic, cytostatic, cytotoxic, antiangiogenic, antirestenotic, microtubule inhibiting, antimigrative or antithrombotic active substances. Examples of antiproliferative, antiinflammatory, antiphlogistic, antihyperplastic, antineoplastic, antimitotic, cytostatic, cytotoxic, antiangiogenic, antirestenotic, microtubule inhibiting, antimigrative or antithrombotic active substances are: abciximab, acemetacin, acetylvismione B, aclarubicin, ademetionine, adriamycin, aescin, afromoson, akagerine, aldesleukin, amidorone, aminoglutethemide, amsacrine, anakinra, anastrozole, anemonin, anopterine, antimycotics, antithrombotics, apocymarin, argatroban, aristolactam-AII, aristolochic acid, arsenic trioxide and other compounds containing arsenic, ascomycin, asparaginase, aspirin, atorvastatin, auranofin, azathioprine, azithromycin, baccatine, bafilomycin, basiliximab, bendamustine, benzocaine, berberine, betulin, betulinic acid, bilobol, biolimus, bisparthenolidine, bleomycin, bombrestatin, boswellic acids and their derivatives, bruceanoles A, B and C, bryophyllin A, busulfan, antithrombin, bivalirudin, cadherins, camptothecin, capecitabine, o-carbamoylphenoxyacetic acid, carboplatin, carmustine, celecoxib, cepharanthin, cerivastatin, CETP inhibitors, chlorambucil, chloroquine phosphate, cictoxin, ciprofloxacin, cisplatin, cladribine, clarithromycin, colchicine, concanamycin, coumadin, C-Type natriuretic peptide (CNP), cudraisoflavone A, curcumin, cyclophosphamide, cyclosporine A, cytarabine, dacarbazine, daclizumab, dactinomycin, dapson, daunorubicin, diclofenac, 1,11-dimethoxycanthin-6-one, docetaxel, doxorubicin, dunaimycin, epirubicin, epothilone A and B, erythromycine, estramustine, etoposide, everolimus, filgrastim, fluoroblastin, fluvastatin, fludarabine, fludarabin-5'-dihydrogenphosphate, fluorouracil, folimycin, fosfestrol, gemcitabine, ghalakinoside, ginkgol, ginkgolic acid, glycoside 1a, 4-hydroxyoxycyclophosphamide, idarubicin, ifosfamide, josamycin, lapachol, lomustine, lovastatin, melphalan, midecamycin, mitoxantrone, nimustine, pitavastatin, pravastatin, procarbazin, mitomycin, methotrexate, mercaptopurine, thioguanine, oxaliplatin, bismuth and bismuth compounds or chelates, irinotecan, topotecan, hydroxycarbamide, miltefosine, pentostatine, pegaspargase, exemestane, letrozole, formestane, SMC proliferation inhibitor-2ω, mitoxantrone, mycophenolate mofetil, c-myc antisense, b-myc antisense, β-lapachone, podophyllotoxin, podophyllic acid 2-ethylhydrazide, molgramostim (rhuGM-CSF), peginterferon α-2b, lanograstim (r-HuG-CSF), macrogol, selectin (cytokin antagonist), cytokin inhibitors, COX-2 inhibitor, NFkB, angiopeptin, monoclonal antibodies which inhibit muscle cell proliferation, bFGF antagonists, probucol, prostaglandins, 1-hydroxy-11-methoxycanthin-6-one, scopolectin, NO donors, pentaerythritol tetranitrate, syndnoimines, S-nitrosoderivatives, tamoxifen, staurosporine, β-oestradiol, α-oestradiol, oestriol, oestrone, ethinyloestradiol, medroxyprogesterone, oestradiol cypionates, oestradiol benzoates, tranilast, kamebakaurin and other terpenoids, which are used in the treatment of cancer, verapamil, tyrosine kinase inhibitors (tyrphostins), paclitaxel, paclitaxel derivatives, 6-α-hydroxy paclitaxel, 2'-succinylpaclitaxel, 2'-succinylpaclitaxeltriethanolamine, 2'-glutarylpaclitaxel, 2'-glutarylpaclitaxeltriethanolamine, 2'-O-ester of paclitaxel with N-(dimethylaminoethyl)glutamide, 2'-O-ester of paclitaxel with N-(dimethylaminoethyl)glutamidhydrochloride, taxotere, carbon suboxides (MCS), macrocyclic oligomers of carbon suboxide, mofebutazone, lonazolac, lidocaine, ketoprofen, mefenamic acid, piroxicam, meloxicam, penicillamine, hydroxychloroquine, sodium aurothiomalate, oxaceprol, β-sitosterin, myrtecaine, polidocanol, nonivamide, levomenthol, ellipticine, D-24851 (Calbiochem), colcemid, cytochalasin A-E, indanocine, nocadazole, S 100 protein, bacitracin, vitronectin receptor antagonists, azelastine, guanidyl cyclase stimulator tissue inhibitor of metal proteinase 1 and 2, free nucleic acids, nucleic acids incorporated into virus transmitters, DNA and RNA fragments, plasminogen activator inhibitor-1, plasminogen activator inhibitor-2, antisense oligonucleotides, VEGF inhibitors, IGF-1, active substances from the group of antibiotics such as cefadroxil, cefazolin, cefaclor, cefotixin, tobramycin, gentamycin, penicillins such as dicloxacillin, oxacillin, sulfonamides, metronidazole, enoxoparin, desulphated and N-reacetylated heparin, tissue plasminogen activator, GpIIb/IIIa platelet membrane receptor, factor Xa inhibitor antibodies, heparin, hirudin, r-hirudin, PPACK, protamine, prourokinase, streptokinase, warfarin, urokinase, vasodilators such as dipyramidol, trapidil, nitroprussides, PDGF antagonists such as triazolopyrimidine and seramine, ACE inhibitors such as captopril, cilazapril, lisinopril, enalapril, losartan, thioprotease inhibitors, prostacyclin, vapiprost, interferon α, β and γ, histamine antagonists, serotonin blockers, apoptosis inhibitors, apoptosis regulators such as p65, NF-kB or Bcl-xL antisense oligonucleotides, halofuginone, nifedipine, tocopherol tranilast, molsidomine, tea polyphenols, epicatechin gallate, epigallocatechin gallate, leflunomide, etanercept, sulfasalazine, etoposide, dicloxacillin, tetracycline, triamcinolone, mutamycin, procainimide, retinoic acid, quinidine, disopyramide, flecamide, propafenone, sotolol, naturally and synthetically obtained steroids such as inotodiol, maquiroside A, ghalakinoside, mansonine, strebloside, hydrocortisone, betamethasone, dexamethasone, non-steroidal substances (NSAIDS) such as fenoporfen, ibuprofen, indomethacin, naproxen, phenylbutazone and other antiviral agents such as acyclovir, ganciclovir and zidovudin, clotrimazole, flucytosine, griseofulvin, ketoconazole, miconazole, nystatin, terbinafine, antiprozoal agents such as chloroquine, mefloquine, quinine, furthermore natural terpenoids such as hippocaesculin, barringtogenol-C21-angelate, 14-dehydroagrostistachin, agroskerin, agrostistachin, 17-hydroxyagrostistachin, ovatodiolids, 4,7-oxycycloanisomelic acid, baccharinoids B1, B2, B3 and B7, tubeimoside, bruceantinoside C, yadanziosides N, and P, isodeoxyelephantopin, tomenphantopin A and B, coronarin A, B, C and D, ursolic acid, hyptatic acid A, iso-iridogermanal, maytenfoliol, effusantin A, excisanin A and B, longikaurin B, sculponeatin C, kamebaunin, leukamenin A and B, 13,18-dehydro-6-alpha-senecioyloxychaparrin, taxamairin A and B, regenilol, triptolide, cymarin, hydroxyanopterin, protoanemonin, cheliburin chloride, sinococuline A and B, dihydronitidine, nitidine chloride, 12-beta-hydroxypregnadien-3,20-dione, helenalin, indicine, indicine-N-oxide, lasiocarpine, inotodiol, podophyllotoxin, justicidin A and B, larreatin, malloterin, mallotochromanol, isobutyrylmallotochromanol, maquiroside A, marchantin A, maytansin, lycoridicin, margetine, pancratistatin, liriodenine, bisparthenolidine, oxoushinsunine, periplocoside A, ursolic acid, deoxypsorospermin, psycorubin, ricin A, sanguinarine, manu wheat acid, methylsorbifolin, sphatheliachromen, stizophyllin, mansonine, strebloside, dihydrousambaraensine, hydroxyusambarine, strychnopentamine, strychnophylline, usambarine, usambarensine, liriodenine, oxoushinsunine, daphnoretin, lariciresinol, methoxylariciresinol, syringaresinol, sirolimus (rapamycin), rapamycin combined with arsenic or with compounds of arsenic or with complexes containing arsenic, somatostatin, tacrolimus, roxithromycin, troleandomycin, simvastatin, rosuvastatin, vinblastine, vincristine, vindesine, thalidomide, teniposide, vinorelbine, trofosfamide, treosulfan, tremozolomide, thiotepa, tretinoin, spiramycin, umbelliferone, desacetylvismione A, vismione A and B, zeorin, fasudil. Preferred active substances that can be applied to the catheter balloon are: paclitaxel and other taxanes, rapamycin and other mTOR (mammalian target of rapamycin) inhibitors, methotrexic acid, arsenic or arsenic compounds, bismuth or bismuth compounds or thalidomide.

In the present description and claims the terms "hydrophilicity" and "hydrophobocity" refer, respectively, to high and low affinity with water of a given molecule or compound. These properties are generally evaluated by measuring the contact angle (θ) as better explained in the Experimental Section of the present description. Wettability defines the degree to which a solid will wet and it is determined by the cohesive forces of the liquid molecules among themselves and the adhesive forces that result from the molecular interactions between the liquid and the solid.

Typically, the range limits are the following: 1) if the solid/liquid interaction (S/L) is strong and the liquid/liquid interaction (L/L) is weak, the wettability is complete and the contact angle is θ=0° (complete wettability and thus maximum hydrophilicity); 2) if the solid/liquid interaction (S/L) is weak and the liquid/liquid interaction (L/L) is weak, the wettability is moderate and the contact angle is θ=90°; 3) if the solid/liquid interaction (S/L) is weak and the liquid/liquid interaction (L/L) is strong, the wettability is absent and the contact angle is θ=180° (absence of wettability and thus maximum hydrophobicity). For example, PA12 has a contact angle θ of about 85°; therefore, a surface modification which increases this angular value makes the PA12 material more hydrophobic while a surface modification which decreases this angular value makes the PA12 material more hydrophilic. Examples of hydrophilic groups are —OH, —COOH, —SO$_3$, —PO$_4$, —NH$_2$, —NH$_4^+$. PEG (poly(ethylene glycol)), PEO (polyethylene oxide). Examples of hydrophobic groups are aliphatic carbon chain, such as, for instance, hydrocarbon chains, polyethylene, polypropylene and polyolefin in general, or an aromatic group, such as, for instance, xylene, polystyrene, acrylonitrile butadiene styrene, or fluoropolymers of formula (CF$_2$)$_n$CF$_3$ wherein n=from 1 to 70, such as, for instance, polytetrafluoroethylene (PTFE).

As the present invention finds particular application for the preparation of medical devices, biopolymers are particularly suitable as the polymeric material for manufacturing a balloon catheter.

Within the following disclosure, a biocompatible polymeric material or a biopolymer is intended to encompass those materials which may be suitably placed in contact with a body surface or tissue and especially with the blood, without triggering tissue irritation or the formation of blood clotting or thrombi. Hydrophilic surfaces have in fact been demonstrated to slow the blood macromolecules and corpuscles absorption.

Preferably, the polymeric material which is suitable for the present invention comprises C—H or C—X functional groups, where X is a heteroatom. Preferably, X is selected from the group comprising nitrogen, oxygen, sulphur, phosphorous, boron, chloride, bromine and iodine.

Particularly preferred biocompatible polymers which are suitable for the present invention include, for instance, polyamides, polyester-polyamide copolymers, the polyamide-based copolymers of general formula

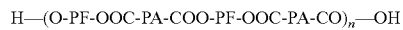

wherein PA is a polyamide segment and PF is a diol segment comprising OH-terminating dimer diol polyesters and n is between 5 and 20 as disclosed in WO 2005/037337 or the polymeric material may be an elastomer obtained by the polymerization of a polyamide forming block compound selected in the group comprising an aminocarboxylic acid of formula (1) below and a lactam of formula (2) below

with a polyetherdiaminic triblock of formula (3) below:

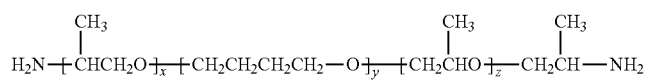

and a dicarboxylic acid of formula (4) below:

wherein R1, R2 and R3 are each binding groups comprising a hydrocarbon chain therein, which may be interrupted by one or more amide groups and wherein R1 and R2 comprise independently an alkylene group having 2 to 20 carbon atoms and amide bonds and R3 comprises an alkylene group having 1 to 20 carbon atoms and wherein x may change from 1 to 20, preferably from 1 to 18, more preferably from 1 to 16, wherein y may change from 4 to 50, preferably from 5 to 45, more preferably from 8 to 30 and z may change from 1 to 20, preferably from 1 to 18, more preferably from 1 to 12 and wherein m is 0 or 1 as disclosed in WO 2007/132485, whose content, with respect to the compounds and preparation methods, is herewith incorporated by reference.

A particularly preferred polymer of the present invention is polyamide and, more in particular, polyamide PA12 and polyether block amide copolymer sold under the trademark PEBAX®.

According to the present invention, the modification of the polymer surface is obtained by the insertion of moieties capable of modifying the wetting properties of the material surface. As shown in FIG. 1, a substituted aromatic azide bearing an R group under UV light produces the extremely reactive intermediate phenylnitrene. Then, the nitrene radical takes a hydrogen from a substrate having C—H bonds thus giving two radical moieties, which then combine together. The result is that the azide molecule is inserted into the substrate.

According to an embodiment of the present invention, the polymeric balloon surface of a balloon catheter is rendered hydrophilic, or at least more hydrophilic than before, by covalently bonding to said surface groups of formula:

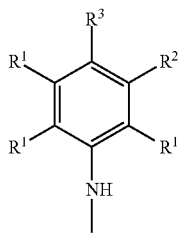

wherein
R$^1$ independently from each is H or F;
R$^2$ is selected from H, F, a Z group selected from —C(O)NH—R$_a$, —S(O)$_2$NH—R$_a$ and —P(O)$_2$NH—R$_a$ wherein R$_a$ is C$_1$-C$_4$ linear or branched saturated alkyl chain optionally substituted with one or more polar functional groups like —OH, —COOH, —SO$_3$, —PO$_4$, —NH$_2$, —NH$_4$+ and the like or with a —(CF$_2$)$_m$—CF$_3$ perfluoroalkyl group wherein m is 1 to 70; or wherein R$_a$ is —(CHRCH$_2$O)$_n$—X wherein n is 1 to 70, R is H or —CH$_3$ and X is selected from H, saturated branched or linear C$_1$-C$_4$ alkyl chain or a —(CH$_2$)$_p$—O—(CH$_2$)$_q$—W group wherein W is H, —CH$_3$ or —NH$_2$ and wherein p and q are independently 1 to 30; or wherein R$_a$ is a C$_1$-C$_{70}$ linear or branched saturated alkyl chain or an aromatic compound; and
R$_3$ is selected from —NO$_2$ or a Z group as above defined.

As per R$_a$ being a linear or branched saturated alkyl chain, it can be selected from the group comprising hydrocarbon chains, polyethylene, polypropylene and polyolefins, while when R$_a$ is an aromatic group, it can be selected among the group comprising xylene, polystyrene and acrylonitrile butadiene styrene.

A preferred perfluoroalkyl R$_a$ group is —(CF$_2$)$_n$CF$_3$, wherein n is 1 to 70 or polytetrafluoroethylene.

As per a preferred embodiment of the invention,
N-(tris(hydroxymethyl)-4-azidobenzenesulphonylamide,
N(-2-hydroxyethyl)-4-azidobenzamide,
N-(2-hydroxyethyl)-4-azidobenzenesulphonylamide,
N-(JEFFAMINE M-600)-4-azidobenzamide,
4-azido-2,3,5,6-tetrafluoro-N-(3-hydroxypropyl)benzamide,
4-azido-2,3,5,6-tetrafluoro-N-(4,4,5,5,6,6,7,7,8,8,9,9,10,10,11,11,11-heptadecafluoroundecyl)benzamide,
2-nitro-5-azidobenzoylglycine,
N-(4,4,5,5,6,6,7,7,8,8,9,9,10,10,11,11,11-heptadecafluoroundecyl) 5-azido-2-nitrobenzoate,
N-(tris(hydroxymethyl)-5-azido-2-nitrobenzoate,
N-(dodecaethylene glycol monomethyl ether)-5-azido-2-nitrobenzoate, and
N-(Hexadecyl)-5-azido-2-nitrobenzoate
have been used for the surface treatment of the balloon polymeric material. JEFFAMINE is a registered trademark for polyoxyalkylene polyamines. JEFFAMINE M600 polyetheramine is a 600 molecular weight polypropylene glycol monoamine, with methoxyethyl termination at the other end and the propylene oxide/ethylene oxide (PO/EO) mol ratio is 9/1. The preparation of said compounds is detailed in the following Experimental Section.

Nevertheless, by changing the composition of the para-substituting R group, in place of the hydrophilic groups mentioned above, suitable hydrophobic moieties can be introduced on the balloon surface of the balloon catheter, as mentioned above.

In case the balloon inner surface has to be modified according to the method of the present invention, the Applicant has found that the photoactivation reaction can be successfully carried out also on the balloon inner surface. To this aim, it is necessary to select the wavelength of the UV light source as well as the polymeric material to be treated so that no absorbance of the radiation may occur. It has been found that the photoactivating wavelength of the above azide compounds does not interfere with the absorbance wavelength of the materials normally used for balloon catheters.

According to an embodiment of the present invention, a solution of methanol or ethanol or acetone or an acetonitrile or a chloroform solution of a para-substituted arylazide compound is prepared and the balloon inner surface to be treated is contacted with said solution. Typically, the solution is made flowing inside the balloon (i.e. within the balloon inner lumen) at the end of the balloon manufacturing process, before the balloon is placed onto and associated to the catheter shaft. Then, the treated surface is activated by light of a suitable wavelength capable of photoactivating the para-substituted arylazide and irradiation is performed for a suitable period of time. Preferably, the light wavelength for a given para-substituted arylazide is selected as the wavelength which substantially corresponds to the maximum absorption for that specific para-substituted arylazide. Typically, the light wavelength is comprised from about 200 nm to about 600 nm. Preferably, the light wavelength is comprised from about 250 nm to about 350 nm and even more preferably is comprised from about 230 nm to about 300 nm. The photoactivation reaction is carried out in a dark environment, at room temperature, i.e. about 25° C., and the reaction time is typically comprised from 0.5-1 hour.

The Applicant has also found that the photoactivation reaction can also occur by causing the solution of azide compound to flow continuously within the balloon. This aspect is particularly advantageous since a continuous process avoids all the drawbacks that are typical of a batch process, in particular in terms of time and costs savings, as well as in terms of uniformity and homogeneity of the treated surface.

Before the photoreaction treatment, the balloon inner surface is preferably washed in order to remove any impurities from the surface. Typically, after the photoreaction treatment has occurred, the balloon inner surface is washed again until all the unbound molecules have been removed. Monitoring of the washing solution is generally carried out by UV.

As said above, in case the inner surface of a balloon is modified, it is necessary that the irradiating UV light passes through the polymeric material of the balloon and reaches the balloon inner surface where the activation process occurs. Therefore, the polymeric material of the balloon must be transparent to the specifically used UV irradiating light.

Preferably, the light wavelength is comprised within the visible spectra and is selected according to the activating molecule used. According to an embodiment of the present invention, the wavelength of maximum absorbance of the substituted arylazide compound is used. For instance, a 254 nm wavelength can be advantageously used since the polymeric materials typically used in the manufacture of balloons are transparent to this light wavelength.

The extent of the modification of the balloon surface treated according to the present invention as well as the modification of the wetting properties of said surface have been evaluated by measuring the Dynamic Contact Angle (DCA) with the Wilhelmy Method, as described in the following Examples.

As above disclosed, the balloon outer surface of a balloon catheter can be modified in order to impart hydrophilic or hydrophobic properties as well as to allow the bound of any suitable active substance.

In order to modify the balloon outer surface, the solution of azide compound can be applied to the balloon surface by any known technique, e.g. dipping, spraying, pipeting, brushing.

Also for the modification of the balloon outer surface, before the photoreaction treatment, the balloon outer surface is preferably washed in order to remove any impurities from the surface. Typically, after the photoreaction treatment has occurred, the balloon outer surface is washed again until all the unbound molecules have been removed.

Example 1

Preparation of N-(tris(hydroxymethyl)-4-azidobenzenesulphonylamide

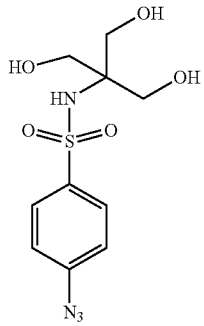 [SMILES: [N-]=[N+]=Nc1ccc(S(=O)(=O)NC(CO)(CO)CO)cc1]

The first step for the preparation of the title compound followed the disclosure of G. A. Wiese e J. W. Jones "Preparation of Tris(hydroxymethyl) sulfanilamidomethane", *Journal of the American Pharmaceutical Association, S.E.*, Volume 37, Issue 9, 380-383 (1948).

In a two-necked flask, 2 moles of 2-amino-2(hydroxymethyl)-1,3-propanediol (TRIS) were solubilised in a minimum amount of water. Then, 1 mole of acetamidobenzenesulphonyl chloride was added. The reaction was left at 70° C. for about half an hour checking the reaction by thin layer chromatography (TLC) with t-butanol-ethyl acetate 2:8 as eluting agent. The substituted amide was treated with a 4-6 N HCl solution in a 1/1.4 molar ratio at 70-80° C. under reflux for about 5 hours. The reaction was checked by TLC with t-butanol-ethyl acetate 2:8 as eluting agent until the starting compound disappeared.

The solvent was then evaporated until a yellowish gel was obtained. The latter was treated with the minimum amount of ethanol in order to solubilise, except for the TRIS chloridrate. Then, water-heating was continued until complete solubilisation, followed by quenching and filtration. The alcoholic solution was treated with gaseous ammonia until a white precipitate of ammonia chloride was obtained. Then a filtration step was carried out and the filtered mixture was left overnight in a refrigerator.

A white precipitate of N-(tris(hydroxymethyl))-4-aminobenzenesulphanylamide was obtained, which was filtered and re-crystallized with an ethanol-water solution 9:1.

The melting point of the filtered and re-crystallized precipitate was 158° C. This value was in accordance with the values mentioned in literature (about 159-161° C.)

The title compound was then prepared by solubilising the N-(tris(hydroxymethyl))-4-aminobenzenesulphanylamide in an aqueous solution of chloride acid (rate 5:1) and was stirred for 15 min in an ice bath at 0° C. Then, a solution obtained dissolving sodium nitrite in the minimum amount of water (nitrite:aniline rate 1:1) was added dropwise bringing the temperature to −5/−10° C. with an ice bath. Then, the reaction was left for 30 min under stirring. The $NaN_3$ was solubilised (molar ratio sodium azide:aniline 1:3) into the minimum water amount and then quenched. It was then added dropwise to the solution and was left reacting for hour at room temperature under stirring. A white precipitate formed, which was filtered and re-crystallized with aqueous methanol (1:1 solution).

The title compound was characterized according to the following analyses (melting point, IR, H-NMR, C-NMR and UV), the description of which is given, for instance, in "*Foundations of Spectroscopy*", S. Duckett and B. Gilbert, Oxford University Press, 2000.

The melting point of the filtered and re-crystallized precipitate was 125° C.

The characteristic peaks of the IR (NaCl) spectrum of the title compound were: 3280 $cm^{-1}$, 2110 $cm^{-1}$, 2130 $cm^{-1}$, 1590 $cm^{-1}$, 1288 $cm^{-1}$, 1054 $cm^{-1}$.

The characteristic peaks of the H-NMR (DMSO) spectrum of the title compound (at 300 MHz) were: 3.43 (s, 6H); 4.2 (br, 3H); 6.92 (s, 1H); 7.25 (2H, d); 7.87 (2H, d).

The characteristic peaks of the C-NMR (DMSO) spectrum of the title compound (at 300 MHz) were: 60.8 (CH2); 64.5, 119.2 (CH); 128.2 (CH); 140.7; 142.8.

The characteristic peaks of the UV (MeOH) spectrum of the title compound were: 208 (4.06); 263 (4.07); 290 (sh, 3.40).

Example 2

Preparation of N(-2-hydroxyethyl)-4-azidobenzamide

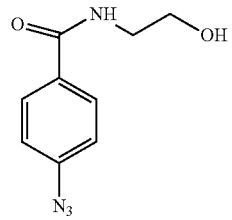 [SMILES: [N-]=[N+]=Nc1ccc(C(=O)NCCO)cc1]

The synthesis followed the description of the process disclosed by H. Brintzinger and H. Koddebusch, "Amid- und Ester-amid-Bildung zwischen carbonsäurechloriden und Mono-, Di- und Triäthanolamin", *Chemische Berichte* 82, 201 (1949).

1 mole quantity of p-nitrobenzoylchloride was dissolved into the minimum quantity of chloroform and equivalent moles of ethanolamine in chloroform (about the same volume). The two solutions were added dropwise to a solution of 2 ml of chloroform within a flask under stirring conditions and under room temperature. The temperature was kept below 40° C. with an ice bath. A white crystalline solid of 4-nitro-N-(2-hydroxyethyl)benzamide formed (yield 90%) which was filtered under pressure and re-crystallized (100% ethylacetate).

The melting point of the filtered and re-crystallized precipitate was 123° C. This value was in accordance with the values mentioned in literature (about 123-125° C.)

Then, the 4-nitro-N-(2-hydroxyethyl)benzamide was solubilised in ethanol and Pd/C was added as the catalyst (Pd/C: 4-nitro-N-(2-hydroxyethyl)benzamide 1:5 weight). In a hydrogenation Erlenmeyer flask the catalyst was placed on the bottom of the flask, then the 4-nitro-N-(2-hydroxyethyl)benzamide and 25 ml of ethanol were added. The mixture was stirred and connected to the hydrogenator. Hydrogen was fluxed into the alcoholic solution under stirring conditions and under atmospheric pressure. Hydrogenation was checked following the hydrogen consumption. At the end of the hydrogenation, filtration was made on filter paper and solvent removed with a rotary evaporator. An oily residue was obtained which crystallized under cooling. A white solid was obtained which was crystallized in 100% ethyl acetate. A white crystalline solid of 4-amino-N-(2-hydroxyethyl)benzamide was obtained.

The melting point of the filtered and re-crystallized precipitate was 119° C. This value was in accordance with the values mentioned in literature (about: 119-120° C.)

The title compound was then obtained by solubilising the 4-amino-N-(2-hydroxyethyl)-benzamide into an aqueous solution of chloridic acid (rate 5:1) and was stirred for 15 min in an ice bath at 0° C. Then, a solution obtained dissolving sodium nitrite in the minimum amount of water (nitrite:aniline rate 1:1) was added dropwise bringing the temperature to −5/−10° C. with an ice bath. Then, the reaction was left for 30 min under stirring. The $NaN_3$ was solubilised (molar ratio sodium azide:aniline 1:3) into the minimum water amount and then quenched. It was then added dropwise to the solution and was left reacting for 1 hour at room temperature under stirring. A white precipitate formed, which was filtered and re-crystallized with aqueous methanol (1:1 solution). The title compound was characterized according to the following analyses (melting point, IR, H-NMR, C-NMR and UV), the description of which is given, for instance, in "*Foundations of Spectroscopy*", S. Duckett and B. Gilbert, Oxford University Press, 2000.

The melting point of the filtered and re-crystallized precipitate was 97-98° C.

The characteristic peaks of the IR (NaCl) spectrum of the title compound were: 3305 $cm^{-1}$, 2132 $cm^{-1}$, 2110 $cm^{-1}$, 1634 $cm^{-1}$, 1284 $cm^{-1}$, 1058 $cm^{-1}$.

The characteristic peaks of the H-NMR (DMSO) spectrum of the title compound (at 300 MHz) were: 3.30 (q, 2H); 3.50 (q, 2H); 7.2 (d, 2H); 7.9 (d, 2H); 8.45 (t).

The characteristic peaks of the C-NMR (DMSO) spectrum of the title compound (at 300 MHz) were: 42.2 (CH2); 59.7 (CH2); 118.8 (CH); 129.1 (CH); 131.1; 142.1; 165.3.

The characteristic peaks of the UV (MeOH) spectrum of the title compound were: 211 (4.23); 268 (4.27); 290 (sh, 378).

Example 3

Preparation of N-(2-hydroxyethyl)-4-azidobenzenesulphonylamide

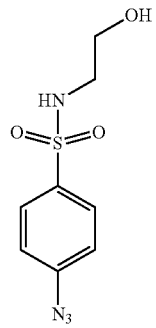 [SMILES: [N-]=[N+]=Nc1ccc(S(=O)(=O)NCCO)cc1]

The synthesis followed the description of the process as disclosed by M. L. Crossley, E. H. Northey, M. E. Hultquist, "Sulfanilamide Derivatives. VI. Substituted N-Aliphatic Sulfaniamides" *J. Am. Chem. Soc.*, 62 (3), pp. 532-534 (1940) with some modifications.

1 mole of p-nitrobenzenesulphonyl chloride was solubilised into the minimum amount of chloroform and equivalent moles of ethanolamine in chloroform (about the same volume).

The two solutions were added dropwise to a solution of 2 ml of chloroform within a flask under stirring conditions and under room temperature. The temperature was kept below 40° C. with an ice bath. A red crystalline solid of N-(2-hydroxyethyl)-4-nitrobenzenesulphonamide formed (yield 68%) which was filtered under pressure and re-crystallized (100% ethylacetate).

The melting point of the filtered and re-crystallized precipitate was 127° C. This value was in accordance with the values mentioned in literature (about 126-127° C.)

1 mole of N-(2-hydroxyethyl)-4-nitrobenzenesulphonamide was dissolved in ethanol into a Erlenmeyer flask and Pd/C was added as the catalyst (N-(2-hydroxyethyl)-4-nitrobenzenesulphonamide:Pd/C 5:1 weight ratio). Successively, in the Erlenmeyer flask the catalyst was placed on the bottom, and then the N-(2-hydroxyethyl)-4-nitrobenzenesulphonamide and 25 ml of ethanol were added. The mixture was stirred and connected to the hydrogenator. Hydrogen was fluxed into the alcoholic solution under stirring conditions and under atmospheric pressure. Hydrogenation was checked following the hydrogen consumption. At the end of the hydrogenation, filtration was made on filter paper and solvent removed with a rotary evaporator. An oily residue was obtained which crystallized under cooling. A brownish-yellowish solid was obtained which was re-crystallized in 100% ethyl acetate. A brownish-yellowish crystalline solid of N-(2-hydroxyethyl)-4-aminobenzenesulphonamide was obtained.

The melting point of the filtered and re-crystallized precipitate was 95° C. This value was in accordance with the values mentioned in literature (about 95-97° C.)

The title compound was prepared solubilising the N-(2-hydroxyethyl)-4-aminobenzenesulphonamide into an aqueous solution of chloridic acid (rate 5:1) and was stirred for 15 min in an ice bath at 0° C. Then, a solution obtained dissolving sodium nitrite in the minimum amount of water (nitrite:aniline rate 1:1) was added dropwise bringing the temperature to −5/−10° C. with an ice bath. Then, the reaction was left for 30 min under stirring. The $NaN_3$ was solubilised (molar ratio sodium azide:aniline 1:3) into the minimum water amount and then quenched. It was then added dropwise to the solution and was left reacting for hour at room temperature under stirring. A white precipitate formed, which was filtered and re-crystallized with aqueous methanol (1:1 solution).

The title compound was characterized according to the following analyses (melting point, IR, H-NMR, C-NMR and UV, the description of which is given, for instance, in "*Foundations of Spectroscopy*", S. Duckett and B. Gilbert, Oxford University Press, 2000.

The melting point of the filtered and re-crystallized precipitate was 57-58° C.

The characteristic peaks of the IR (NaCl) spectrum of the title compound were: 3445 $cm^{-1}$, 2134 $cm^{-1}$, 2115 $cm^{-1}$, 1588 $cm^{-1}$, 1301 $cm^{-1}$, 1160 $cm^{-1}$.

The characteristic peaks of the H-NMR (DMSO) spectrum of the title compound (at 300 MHz) were: 2.77 (q, 2H); 3.36 (t, 2H); 4.8 (br, 1H); 7.32 (8d, 2H); 7.64 (t, 1H); 7.47 (d, 2H).

The characteristic peaks of the C-NMR (DMSO) spectrum of the title compound (at 300 MHz) were: 45.0 (CH2); 59.8 (CH2); 119.7 (CH2); 128.5 (CH2); 136.8; 143.5.

The characteristic peaks of the UV (MeOH) spectrum of the title compound were: 210 (4.30); 263 (4.40); 290 (sh, 2.45).

Example 4

Preparation of N-(JEFFAMINE M-600)4-azidobenzamide

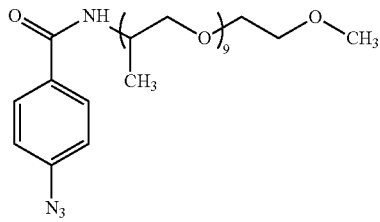

p-nitrobenzoylchloride was dissolved into the minimum quantity of chloroform and equivalent moles of JEFFAMINE M600 (Jefferson Chemical Co.) of formula

Figure 2:
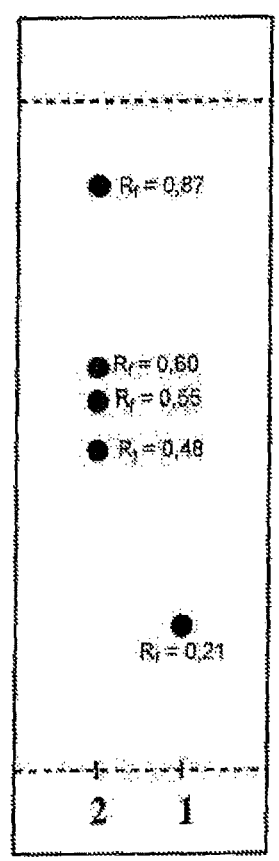
FIG. 2 shows the TLC obtained for the preparation of a compound according to EXAMPLE 4.

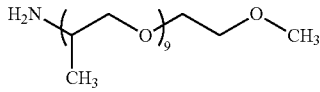

into chloroform. The two solutions were added dropwise to a solution of 2 ml of chloroform within a flask under stirring conditions and under room temperature. The reaction was left for 24 h checking the reaction by TLC in 100% ethylacetate until no p-nitrobenzoilchloride is detected in the reaction mixture. The solvent is evaporated with rotary evaporator and a yellowish syrup-like oil is obtained. By TLC (ethyl acetate/cycloesane 8/2) four reaction products are detected as shown in FIG. 2, wherein line 1 corresponds to p-nitrobenzoilchloride and line 2 corresponds to the reaction products. The reaction product was directly loaded onto silica gel after flash chromatography as a brown oil.
Chromatography Column:
Diameter: 5 cm
Fixed phase: neutral alumina—12 cm high
Mobile phase: cycloesane The oil is solubilised into the minimum quantity of cycloesane and is deposited in the column.

The first eluted compound (Rf TLC: 0.87) is the white crystalline solid of ethyl-4-nitrobenzoate; the other three eluted products all are N-(JEFFAMINE M-600)-4-nitrobenzamide.

The title compound was characterized according to the following analyses (IR, H-NMR, C-NMR), the description of which is given, for instance, in "*Foundations of Spectroscopy*", S. Duckett and B. Gilbert, Oxford University Press, 2000.

The characteristic peaks of the IR (NaCl) spectrum of the title compound were: 3325 cm$^{-1}$, 2975 cm$^{-1}$, 1653 cm$^{-1}$, 1602 cm$^{-1}$, 1527 cm$^{-1}$, 1346 cm$^{-1}$, 1107 cm$^{-1}$.

The characteristic peaks of the H-NMR (CDCl$_3$) spectrum of the title compound (at 300 MHz) were: 1.1 (m, ca. 21H); 3.3 (s, 3H); 3.3, 3.7 (m, ca. 22H); 8.0 (m, 2H); 8.23 (d, 2H).

The characteristic peaks of the C-NMR (CDCl$_3$) spectrum of the title compound (at 300 MHz) were: ca. 17 (6 CH3); 59.0 (CH3); 71.5, 73.4 (5 CH2); 74.7, 75.3 (5 CH); 123.3, 123.4 (CH); 18.4 (3 CH); 140.4 (2 C); 149.3; 164.5; 164.8.

N-(JEFFAMINE M-600)-4-nitrobenzamide was solubilised in ethanol and Pd/C was added as the catalyst (N-(JEFFAMINE M-600)-4-nitrobenzamide:Pd/C 5:1 weight ratio).

Then, in the Erlenmeyer flask the catalyst was placed on the bottom, then the N-(JEFFAMINE M-600)-4-nitro benzamide and 25 ml of ethanol. The mixture was stirred and connected to the hydrogenator. Hydrogen was fluxed into the alcoholic solution under stirring conditions and under atmospheric pressure. Hydrogen was checked following the hydrogen consumption. At the end of the hydrogenation, filtration was made on filter paper and solvent removed with rotary evaporator. A yellowish-brownish oil is obtained.

The title compound was characterized according to the following analyses (IR, H-NMR), the description of which is given, for instance, in "*Foundations of Spectroscopy*", S. Duckett and B. Gilbert, Oxford University Press, 2000.

The characteristic peaks of the IR (NaCl) spectrum of the title compound were: 3355 cm$^{-1}$, 2972 cm$^{-1}$, 1634 cm$^{-1}$, 1608 cm$^{-1}$, 1506 cm$^{-1}$, 1105 cm$^{-1}$.

The characteristic peaks of the H-NMR (CDCl$_3$) spectrum of the title compound (at 300 MHz) were: 1.15, 1.25 (ca. 30H, m); 3.45 (s, 3H); 3.3, 3.8 (ca. 36H, m); 6.82 (m, 2H); 7.70 (m, 2H).

Then, N-(JEFFAMINE M-600)-4-aminobenzamide was solubilised into an aqueous solution of chloridic acid (rate 5:1) and was stirred for 15 min in an ice bath at 0° C. Then, a solution obtained dissolving sodium nitrite in the minimum amount of water (nitrite:aniline rate 1:1) was added dropwise bringing the temperature to −5/−10° C. with an ice bath. Then, the reaction was left for 30 min under stirring. The NaN$_3$ was solubilised (molar ratio sodium azide:aniline 1:3) into the minimum water amount and then quenched. It was then added dropwise to the solution and was left reacting for 1 hour at room temperature under stirring. Two phases formed by adding chloroform: a yellowish oil was obtained.

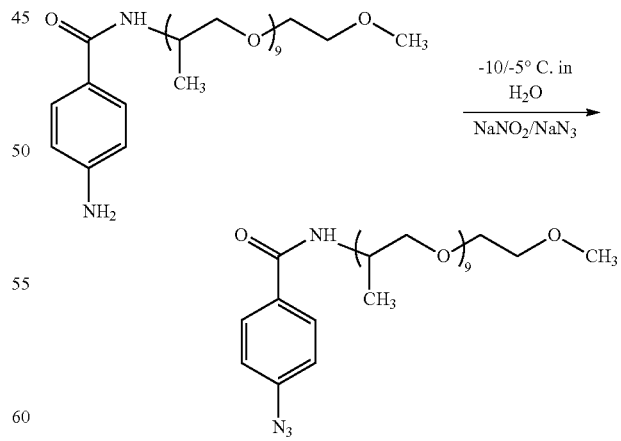

The title compound was characterized according to the following analyses (IR, H-NMR, C-NMR), the description of which is given, for instance, in "*Foundations of Spectroscopy*", S. Duckett and B. Gilbert, Oxford University Press, 2000.

The characteristic peaks of the IR (NaCl) spectrum of the title compound were: 3350 cm$^{-1}$, 2972 cm$^{-1}$, 2123 cm$^{-1}$, 1654 cm$^{-1}$, 1688 cm$^{-1}$, 1604 cm$^{-1}$, 1499 cm$^{-1}$, 1275 cm$^{-1}$, 1109 cm$^{-1}$.

The characteristic peaks of the H-NMR (CDCl$_3$) spectrum of the title compound (at 300 MHz) were: 1.15 (m, 21H); 3.4 (s, 3H); 3.4, 3.7 (m, 23H); 7.4 (d, 2H); 7.8, 7.9 (m, 2H).

The characteristic peaks of the C-NMR (CDCl$_3$) spectrum of the title compound (at 300 MHz) were: 17 (6 CH3); 58.9 (CH3); 72 (5 CH); 74 (4 CH2); 118.7 (CH); 128 (2 CH); 131.3, 142.9, 165.5 (2 C).

Example 5

Preparation of 4-azido-2,3,5,6-tetrafluoro-N-(3-hydroxypropyl)benzamide

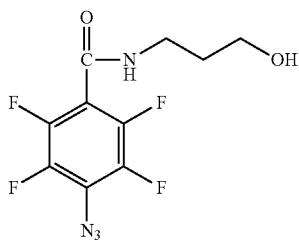 [SMILES: [N-]=[N+]=Nc1c(F)c(F)c(C(=O)NCCCO)c(F)c1F]

The synthesis followed the description of the process disclosed by "Facile UV Patterning of Robust Carbon Nanotube Forests Using Perfluoroarylazides"; S. J. Pastine, D. Okawa, B. Kessler, M. Rolandi, M. Llorente, A. Zettl, and J. M. J. Frechet; *J. AM. CHEM. SOC.* 2008, 130, 4238-4239.

In an two-necked flask were placed succinimidyl-(4-azido tetrafluoro)benzoate (204 mg, 0.614 mmol, 1.0 equiv.) and mL of CH$_2$Cl$_2$. To the resulting solution was added proponolamine (60 μL, 0.737 mmol, 1.2 equiv.) via syringe.

After 2 h, the reaction was diluted with CH$_2$Cl$_2$, washed with water (twice), brine, dried over magnesium sulfate, and concentrated in vacuum to give a off-white/pinkish solid in a quantitative yield, i.e. with a yield of about 100%. The compound can be further purified via flash chromatography (hexanes/ethyl acetate=1:2) to give a white solid.

The title compound was characterized according to the following analyses (melting point, IR, H-NMR, UV), the description of which is given, for instance, in "*Foundations of Spectroscopy*", S. Duckett and B. Gilbert, Oxford University Press, 2000.

The melting point of the compound was 95° C.-100° C.

The characteristic peaks of the IR (NaCl) spectrum of the title compound were: 3276 cm$^{-1}$; 2133 cm$^{-1}$; 1656 cm$^{-1}$.

The characteristic peaks of the H-NMR (CDCl$_3$) spectrum of the title compound (at 300 MHz) were: 6.6 (NH); 3.8 (CH$_2$OH); 3.6 (CH$_2$NH); 2.9 (OH); 1.9 (CH$_2$).

The characteristic peak of the UV (MeOH) spectrum of the title compound was 256 nm.

Example 6

Preparation of 4-azido-2,3,5,6-tetrafluoro-N-(4,4,5,5,6,6,7,7,8,8,9,9,10,10,11,11,11-heptadecafluoroundecyl)benzamide

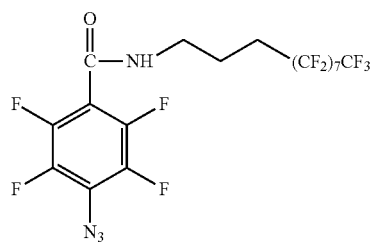

The synthesis followed the description of the process disclosed by "Facile UV Patterning of Robust Carbon Nanotube Forests Using Perfluoroarylazides"; S. J. Pastine, D. Okawa, B. Kessler, M. Rolandi, M. Llorente, A. Zettl, and J. M. J. Frechet; *J. AM. CHEM. SOC.* 2008, 130, 4238-4239.

In an two-necked flask were placed succinimidyl-(4-azido tetrafluoro)benzoate (100 mg, 0.300 mmol, 1.0 equiv.), 2 mL of CH$_2$Cl$_2$, and 2 mL ethyl acetate. To the resulting solution was added 4,4,5,5,6,6,7,7,8,8,9,9,10,10,11,11,11-heptadecafluoroundecylamine (150 mg, 0.314 mmol, 1.05 equiv.) via syringe.

After 4 h, the reaction suspension was directly loaded on to silica gel after flash chromatography (hexanes:ethyl acetate=2:1 then 1:1) as a white solid.

The title compound was characterized according to the following analyses (melting point, IR, H-NMR, UV), the description of which is given, for instance, in "*Foundations of Spectroscopy*", S. Duckett and B. Gilbert, Oxford University Press, 2000.

The melting point of the obtained solid was 100° C.-102° C.

The characteristic peaks of the IR (NaCl) spectrum of the title compound were: 2127 cm$^{-1}$; 1654 cm$^{-1}$; 1147 cm$^{-1}$.

The characteristic peaks of the H-NMR (CDCl$_3$) spectrum of the title compound (at 300 MHz) were: 6.1 (NH); 3.55 (CH$_2$NH); 2.20 (CH$_2$(CF$_2$)$_7$); 1.95 (CH$_2$—CH$_2$—CH$_2$).

The characteristic peak of the UV (MeOH) spectrum of the title compound was 256 nm.

Example 7

Preparation of 2-nitro-5-azidobenzoylglycine

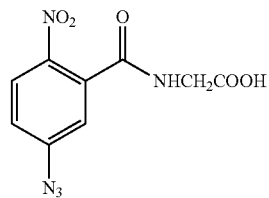

The synthesis followed the description of the process disclosed by "Photoaffinity Labeling of Peptide Hormone Binding Sites"; R. E. Galardy, L. C. Craig, J. D. Jamieson and M. P. Printz; *The Journal of Biological Chemistry*, Vol. 249, No. 11, PP. 2510-2618, 1974.

To 2.5 g of sodium bicarbonate and 1.1 g of glycine in 70 ml of water was added 3.9 g of the N-hydroxysuccinimide ester of 4-azidobenzoic acid in 140 ml of dioxane. After hour the mixture was rotary evaporated to 40 ml, cooled in ice, and adjusted to pH 2 with concentrated hydrochloric acid. All procedures were done in darkness. The solid product was re-crystallized from water.

The title compound was characterized according to the following analyses (melting point, IR, H-NMR, C-NMR and UV), the description of which is given, for instance, in "*Foundations of Spectroscopy*", S. Duckett and B. Gilbert, Oxford University Press, 2000.

The melting point of the filtered and re-crystallized precipitate was 189° C.-195° C.

The characteristic peaks of the IR (NaCl) spectrum of the title compound were: 3287 cm$^{-1}$; 2102 cm$^{-1}$; 1704 cm$^{-1}$; 1644 cm$^{-1}$; 1582 cm$^{-1}$.

The characteristic peaks of the H-NMR (DMSO) spectrum of the title compound (at 300 MHz) were: 12.35 (OH); 9.0 (NH); 8.1, 7.4, 7.2 (aromatic H); 3.9 (CH$_2$).

The characteristic peaks of the C-NMR (DMSO) spectrum of the title compound (at 300 MHz) were: 170, 164 (C=O); 145, 143, 134, 126, 120, 118 (aromatic H); 40 (CH$_2$).

The characteristic peaks of the UV (MeOH) spectrum of the title compound was 307 nm.

Example 8

Preparation of N-(4,4,5,5,6,6,7,7,8,8,9,9,10,10,11,11,11-heptadecafluoroundecyl) 5-azido-2-nitrobenzoate In an two-necked flask were placed N-succinimidyl-5-azido-2-nitrobenzoate (100 mg) and 4,4,5,5,6,6,7,7,8,8,9,9,10,10,11,11,11-heptadecafluoroundecylamine (180 mg) in 3 mL of ethyl acetate.

The solution was placed in darkness to stir overnight.

The reaction product was directly loaded on to silica gel after flash chromatography (hexanes:ethyl acetate=2:1) as a white solid.

The title compound was characterized according to the following analyses (melting point, IR, H-NMR, C-NMR and UV), the description of which is given, for instance, in "*Foundations of Spectroscopy*", S. Duckett and B. Gilbert, Oxford University Press, 2000.

The melting point of the filtered and re-crystallized precipitate was 105-110° C.

The characteristic peaks of the IR (NaCl) spectrum of the title compound were: 3260 cm$^{-1}$; 2100 cm$^{-1}$; 1640 cm$^{-1}$; 1200 cm$^{-1}$; 1100 cm$^{-1}$.

The characteristic peaks of the H-NMR (DMSO) spectrum of the title compound (at 300 MHz) were: 8.75 (NH); 8.1, 7.4, 7.25 (aromatic H); 2.45, 1.75 (aliphatic H).

The characteristic peaks of the C-NMR (DMSO) spectrum of the title compound (at 300 MHz) were: 165 (C=O); 145, 142, 135, 125, 120, 118 (aromatic C); 40, 30, 20 (aliphatic H).

The characteristic peaks of the UV (MeOH) spectrum of the title compound was 308 nm.

Example 9

Preparation of N-(tris(hydroxymethyl)-5-azido-2-nitrobenzoate

In an two-necked flask were placed N-succinimidyl-5-azido-2-nitrobenzoate (100 mg) and 3.6 mL of dioxane. To the resulting solution was added a solution of tris(hydroxymethyl)aminomethane (80 mg in 1 mL of water) and 200 μL of TEA via syringe.

The solution was placed in darkness to stir overnight.

The sample was brought to dry with a rotary evaporator and vacuum pump (one night). The product was a yellow crystalline solid.

The title compound was characterized according to the following analyses (melting point, IR, H-NMR, C-NMR and UV), the description of which is given, for instance, in "*Foundations of Spectroscopy*", S. Duckett and B. Gilbert, Oxford University Press, 2000.

The melting point of the obtained product was 125-130° C.

The characteristic peaks of the IR (NaCl) spectrum of the title compound were: 3381 cm$^{-1}$; 2124 cm$^{-1}$; 1713 cm$^{-1}$; 1583 cm$^{-1}$; 1410 cm$^{-1}$.

The characteristic peaks of the H-NMR (DMSO) spectrum of the title compound (at 300 MHz) were: 8.1 (NH); 7.4, 7.1, 7.05 (aromatic H); 3.75 (OH); 2.25 (aliphatic H).

The characteristic peaks of the C-NMR (DMSO) spectrum of the title compound (at 300 MHz) were: 165 (C=O); 145, 140, 135, 127, 125, 120 (aromatic C); 62 (C—OH); 25, 35, 40 (aliphatic C).

The characteristic peaks of the UV (MeOH) spectrum of the title compound was 308 nm.

Example 10

Preparation of N-(dodecaethylene glycol monomethyl ether)-5-azido-2-nitrobenzoate In an two-necked flask were placed N-succinimidyl-5-azido-2-nitrobenzoate (100 mg), 5 mL of ethyl acetate and 200 μL of triethylamine. To the resulting solution was added a solution of methyl-PEG$_{12}$-amine (purchased from ThermoFisher Scientific) in ethyl acetate (183 mg in 5 mL) via syringe. The solution was placed in darkness to stir for 16 hours. The solution (bright yellow) was extracted with 10 mL of brine for two times. The water phase was extracted with 10 mL of CH$_2$Cl$_2$ (3 times). The organic phase was dehydrated with anhydrous MgSO$_4$, filtered and brought to dry rotary evaporator. The product is a dark yellow oil.

The title compound was characterized according to the following analyses (melting point, IR, H-NMR, C-NMR and UV), the description of which is given, for instance, in "Foundations of Spectroscopy", S. Duckett and B. Gilbert, Oxford University Press, 2000.

The characteristic peaks of the IR (NaCl) spectrum of the title compound were: 3200 cm$^{-1}$; 2873 cm$^{-1}$; 2121 cm$^{-1}$; 1669 cm$^{-1}$; 1104 cm$^{-1}$.

The characteristic peaks of the H-NMR (CDCl$_3$) spectrum of the title compound (at 300 MHz) were: 6.8 (NH); 8.2, 7.3, 7.2 (aromatic H); 3.65 (aliphatic H); 3.3 (OCH$_3$).

The characteristic peaks of the C-NMR (CDCl$_3$) spectrum of the title compound (at 300 MHz) were: 165 (C=O); 146, 142, 135, 127, 120, 119 (aromatic C); 70 (aliphatic C); 57 (OCH$_3$).

The characteristic peaks of the UV (MeOH) spectrum of the title compound was 305 nm.

Example 11

Preparation of N-(hexadecyl)-5-azido-2-nitrobenzoate

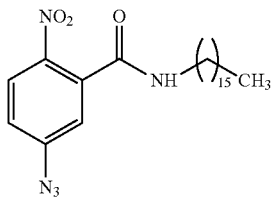

In an two-necked flask were placed N-succinimidyl-5-azido-2-nitrobenzoate (1 g) and hexadecylamine (0.791 g) in 50 mL of ethyl acetate and 30 mL of dichloromethane. 200 μL of triethanolamine where successively added under stirring conditions.

The solution was placed in darkness to stir overnight.

The reaction product was directly loaded onto silica gel after flash chromatography (hexanes:ethyl acetate=2:1) as a white solid.

The title compound was characterized according to the following analyses (melting point, IR, H-NMR, UV), the description of which is given, for instance, in "Foundations of Spectroscopy", S. Duckett and B. Gilbert, Oxford University Press, 2000.

The melting point of the reaction product was 94-100° C.

The characteristic peaks of the IR (NaCl) spectrum of the title compound were: 3278.4 cm$^{-1}$; 2122.2 cm$^{-1}$; 1644.2 cm$^{-1}$.

The characteristic peaks of the H-NMR (DMSO) spectrum of the title compound (at 300 MHz) were: 8.6 (NH); 8.1, 8.05, 7.4, 7.3, 7.2 (aromatic H); 3.2, 0.8 (aliphatic H).

The characteristic peaks of the UV (MeOH) spectrum of the title compound was 305 nm.

Example 12

Determination of Dynamic Contact Angle (DCA)

Typically, the method for measuring molecular interactions is the Dynamic Contact Angle (DCA) test ("Advancing and Receding Contact Angles" using a tilting base). The contact angle is measured on sessile drops by analyzing the profile of the drop and measuring the angle whose vertex begins at the three-phase line. As the solid is tilted from 0° to 90°, the receding angle decreases while the advancing angle increases. The difference between the advancing and receding angle is the Contact Angle Hysteresis. However, since the purpose was to measure the Dynamic Contact Angle (DCA) of a cylindrical profile (i.e. an angioplasty balloon), the method with tilting base could not be used for this type of samples. Therefore, the Dynamic Contact Angle (DCA) of the samples was measured with the Wilhelmy Method according to which a solid sample is held by an electro-balance and pushed into or pulled from a liquid of known surface tension. As the solid sample penetrates into the liquid, an advancing contact angle is determined, while pulling the sample from the liquid provides the receding contact angle measurement.

The Wilhelmy Method is disclosed, for instance, in "Contact Angle Hysteresis on Heterogeneous Surfaces" (Leonard W. Schwartz, Stephen Garoff—Langmuir 1985, 1, 219-230), "Molecular Mechanisms Associated with Adhesion and Contact Angle Hysteresis of Monolayer Surfaces" (Y. L. Chen, C. A. Helm, J. N. Israelachvili—J. Phys. Chem. 1991, 95, 10736-10747), "Dynamic Contact Angles and Contact Angle Hysteresis of Plasma Polymers" (J. H. Wang, P. M. Claesson, J. L. Parker H. Yasuda—Langmuir 1994, 10, 3887-3897), "A Systematic Comparison of Contact Angle Methods" (Lorraine M. Lander, Lisa M. Siewierski, William J. Brittain, Erwin A. Voglert—Langmuir 1993, 9, 2237-2239).

The measurement of the Dynamic Contact Angle (DCA) with the Wilhelmy Method was performed both on:
a) plate samples, and
b) balloon samples
so that the values obtained from the balloon samples (more complex geometry) could be compared with the values obtained from the plate samples (very simple geometry).

Example 12a

Determination of the Dynamic Contact Angle (DCA) with the Wilhelmy Method on Plate Samples In order to define a test protocol, firstly the Dynamic Contact Angle (DCA) of polymeric plates were measured.

The plates were made of polyamide 12 and had the following dimensions: wideness W=25 mm, length L=30 mm and thickness s=1.2 mm.

The measurements were performed with the Force Tensiometer Sigma 700 (manufactured by KSV Instruments, Inc.). The plates were cleaned with methanol and acetone, and successively they were dipped all night in a solution of a specific aromatic azide. The plates were moved into the solution and out of the solution at a speed of 3 mm/min. The plates were immersed into the solution for a depth of 17 mm.

Five different aromatic azides had been tested (as per Table 1 below), while one sample made of PA12 was not treated with any aromatic azide (control sample):

TABLE 1

| | |
|---|---|
| PA12 | Polyamide12 |
| TRIS | N-(tris(hydroxymethyl)-4-azidobenzenesulphonylamide |
| pnPTFE | N-(4,4,5,5,6,6,7,7,8,8,9,9,10,10,11,11,11-heptadecafluoroundecyl)-5-azido-2-nitrobenzoate |
| pnTRIS | N-(tris(hydroxymethyl)-5-azido-2-nitrobenzoate |
| pnPEG | N-(dodecaethylene glycol monomethyl ether)-5-azido-2-nitrobenzoate |
| pnALC | N-(hexadecyl)-5-azido-2-nitrobenzoate |

All the samples were irradiated for 30 minutes with a UV light at a wavelength of 254 nm.

Successively, the irradiated samples were cleaned with a solution of methanol, acetone and water.

After draining for 15 min, the samples were tested with the Force Tensiometer and the results are shown in Table 1.

The PA12 plate (control sample) underwent all the process steps carried out on the azide-treated samples. The only difference was that the solution into which the PA12 plate was immersed did not contain any aromatic azide.

By analyzing the values of Table 2 it is apparent that:

for the hydrophilic molecules (samples S2, S4 and S5 made of TRIS, pnTRIS and pnPEG material respectively) the $\theta_{rec}$ (parameter usable for the study of the polar fraction of a surface) is decreased with respect to the $\theta_{rec}$ value of PA12 per se (sample S1 made of PA12 and not treated with the aromatic azide);

for the hydrophobic molecules (samples S3 and S6 made of pnPTFE and pnALC material respectively) the $\theta_{adv}$ (parameter usable for the study of dispersive fraction of surface) is increased with respect to the $\theta_{adv}$ value of PA12 per se (sample S1 made of PA12 and not treated with the aromatic azide).

Figure 3B:
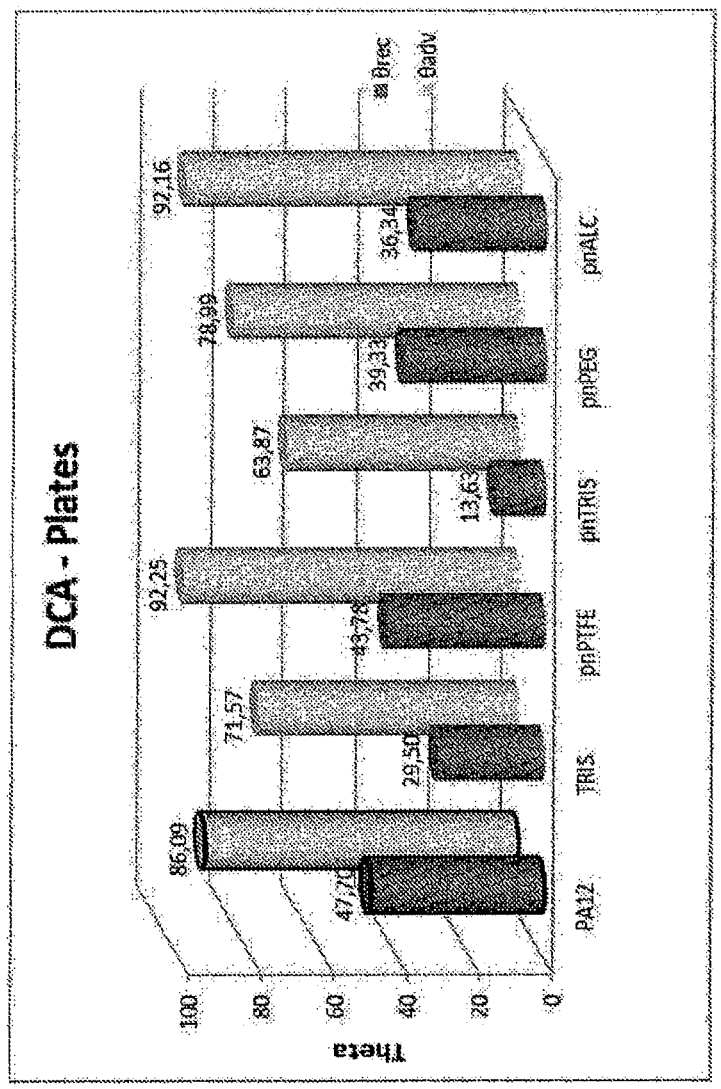
FIG. 3B shows the histogram of the values reported in FIG. 3A (Table 2)

The values of Table 2 are also plotted in FIG. 3 in the form of a histogram.

Figure 4:
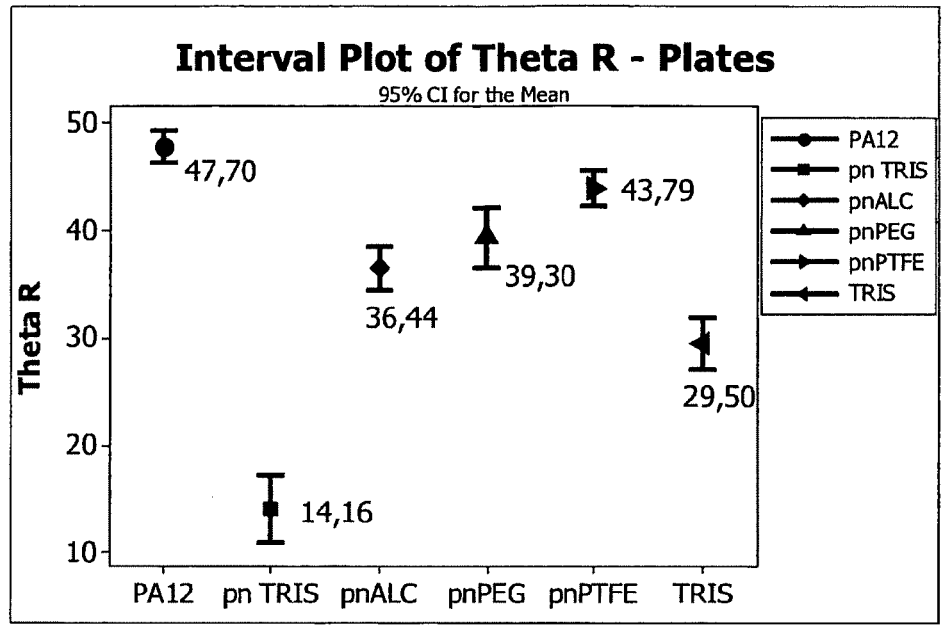
FIGS. 4 and 5 show the plotting of the standard deviation values reported in FIG. 3A (Table 2)
Figure 5:
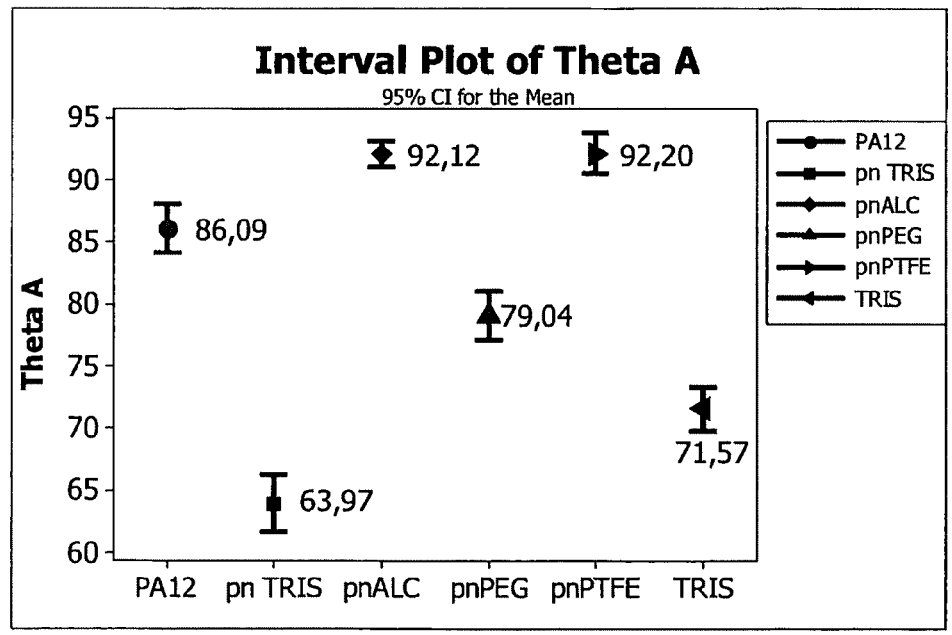

Moreover, FIG. 4 and FIG. 5 show, respectively, the $\theta_{rec}$ and the $\theta_{adv}$ values of Table 2, plotted with indication of their respective standard deviations.

Therefore, Table 2 clearly shows that the surface of the polymeric plates clearly underwent a modification as a consequence of the photoactivation reaction according to the present invention. This is also confirmed by the values reported in Table 3 where it is shown the variation in percentage of the receding and advancing contact angles (θ %) with respect to the receding and advancing contact angles of the non-treated surface (i.e. S1).

Example 12b

Determination of the Dynamic Contact Angle (DCA) with the Wilhelmy Method on Balloon Samples Mole The testing procedure described in Example 12a was used also for testing the balloon samples.

The balloons (ADMIRAL® XTREME manufactured by Invatec S.p.A.) were made of polyamide 12 and had the following dimensions: Outer Diameter=4 mm and Length L=60 mm.

The measurements were performed with the Force Tensiometer Sigma 700 (manufactured by KSV Instruments, Inc.).

The balloons were cleaned with methanol and acetone, and successively they were dipped all night in a solution of a specific aromatic azide.

Two different aromatic azides had been tested (as per the table below), while one sample made of PA12 was not treated with any aromatic azide (control sample):

TABLE 4

| | |
|---|---|
| PA12 | Polyamide12 |
| pnTRIS | N-(tris(hydroxymethyl)-5-azido-2-nitrobenzoate |
| pnALC | N-(hexadecyl)-5-azido-2-nitrobenzoate |

All the samples were irradiated for 30 minutes with a UV light at a wavelength of 254 nm. Successively, the irradiated samples were cleaned with a solution of methanol, acetone and water. After draining for 15 min, the samples were tested with the Force Tensiometer and the results are shown in Table 5. The PA12 balloon (control sample) underwent all the process steps carried out on the azide-treated samples. The only difference was that the solution into which the PA12 balloon was immersed did not contain any aromatic azide.

By analyzing the values of Table 5 it is apparent that:

for the hydrophilic molecule (sample S8 made of pnTRIS material) the $\theta_{rec}$ (parameter usable for the study of the polar fraction of a surface) is remarkably decreased with respect to the $\theta_{rec}$ value of PA12 per se (sample S7 made of PA12 and not treated with aromatic azide);

for the hydrophobic molecule (samples S9 made of pnALC material) the $\theta_{adv}$ (parameter usable for the study of dispersive fraction of surface) is increased with respect to the $\theta_{adv}$ value of PA12 per se (sample S7 made of PA12 and not treated with aromatic azide).

Figure 6B:
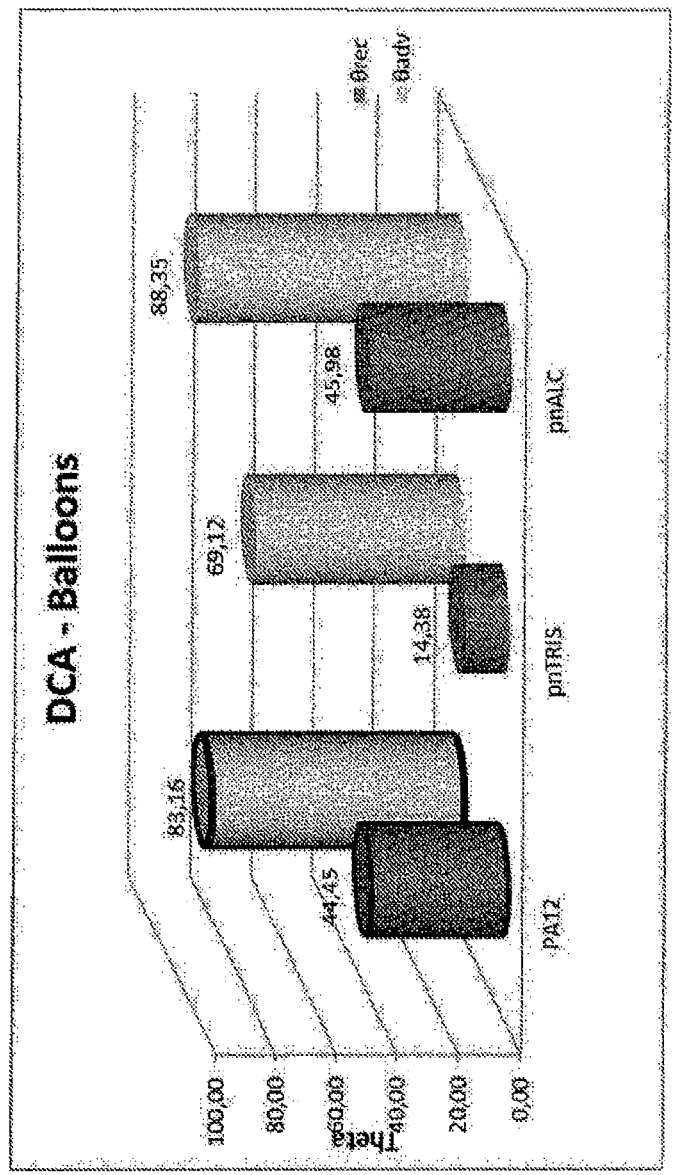
FIG. 6B shows the histogram of the values reported in FIG. 6A (Table 5)

The values of Table 5 are also plotted in FIG. 6 in the form of a histogram.

Figure 7:
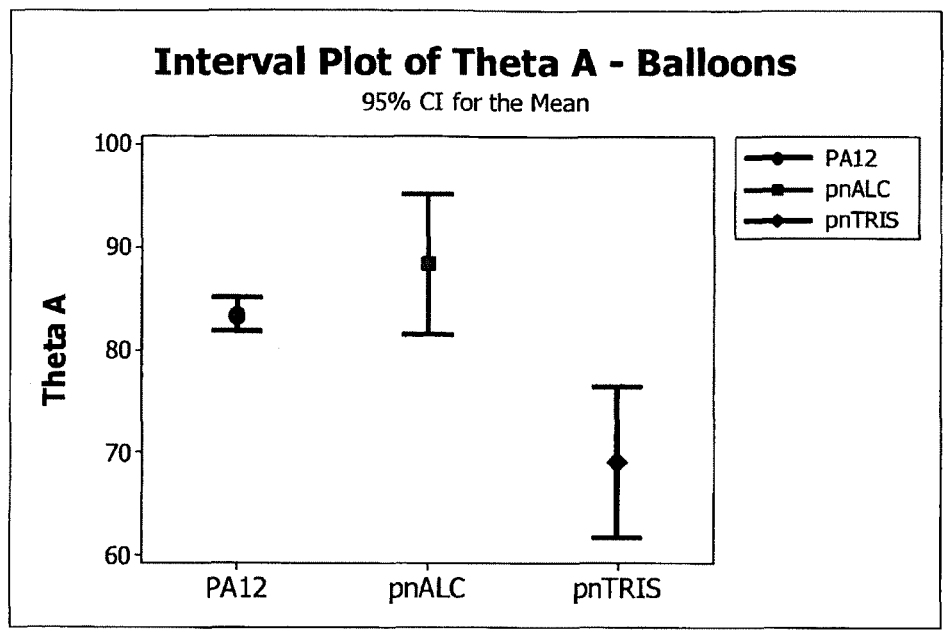
FIGS. 7 and 8 show the plotting of the standard deviation values reported in FIG. 6A (Table 5)
Figure 8:
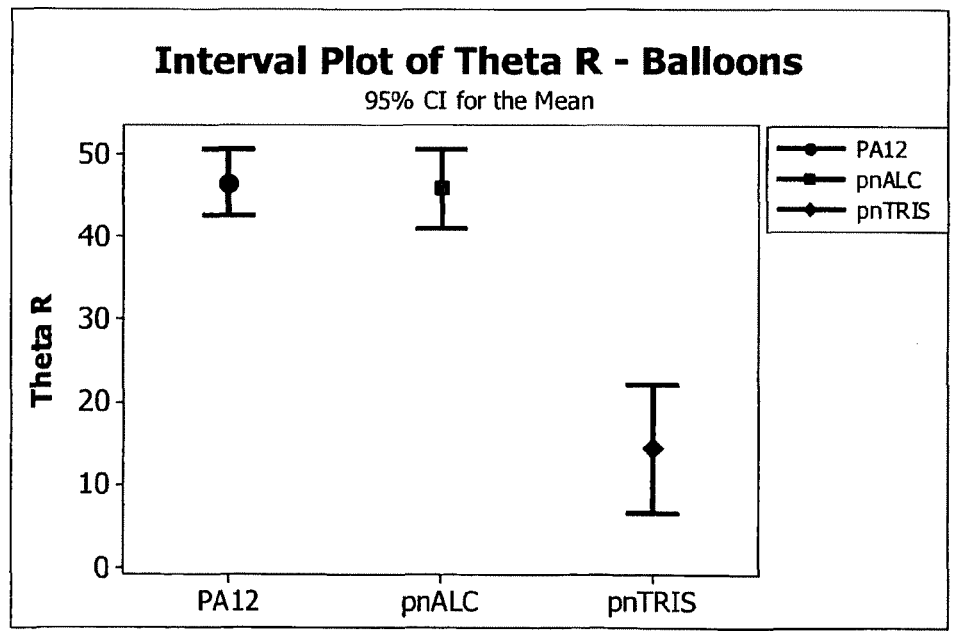

Moreover, FIG. 7 and FIG. 8 show, respectively, the $\theta_{rec}$ and the $\theta_{adv}$ values of Table 5, plotted with indication of their respective standard deviations.

Therefore, Table 5 clearly shows that the surface of the polymeric balloons clearly underwent a modification as a consequence of the photoactivation reaction according to the present invention. This is also confirmed by the values reported in Table 6 where it is shown the variation in percentage of the receding and advancing contact angles (θ %) with respect to the receding and advancing contact angles of the non-treated surface (i.e. S7).

Moreover, for the same materials, by comparing the contact angles obtained for the plate samples and the balloon samples (Table 2 and Table 5), it is apparent that the obtained contact angles after the photoactivation reaction according to the present invention are very similar. This means that the surface modification obtained on a plate sample (flat sample of elementary geometry) was obtained also on a balloon sample (cylindrical sample of much more complex geometry).

Example 13

Evaluation of the Photoactivation Reaction Yield of the Polymeric Surface

This analysis shows how the photoactivation reaction yield of the polymeric surface is influenced by the substituted aromatic azide used for the reaction.

Figure 9:
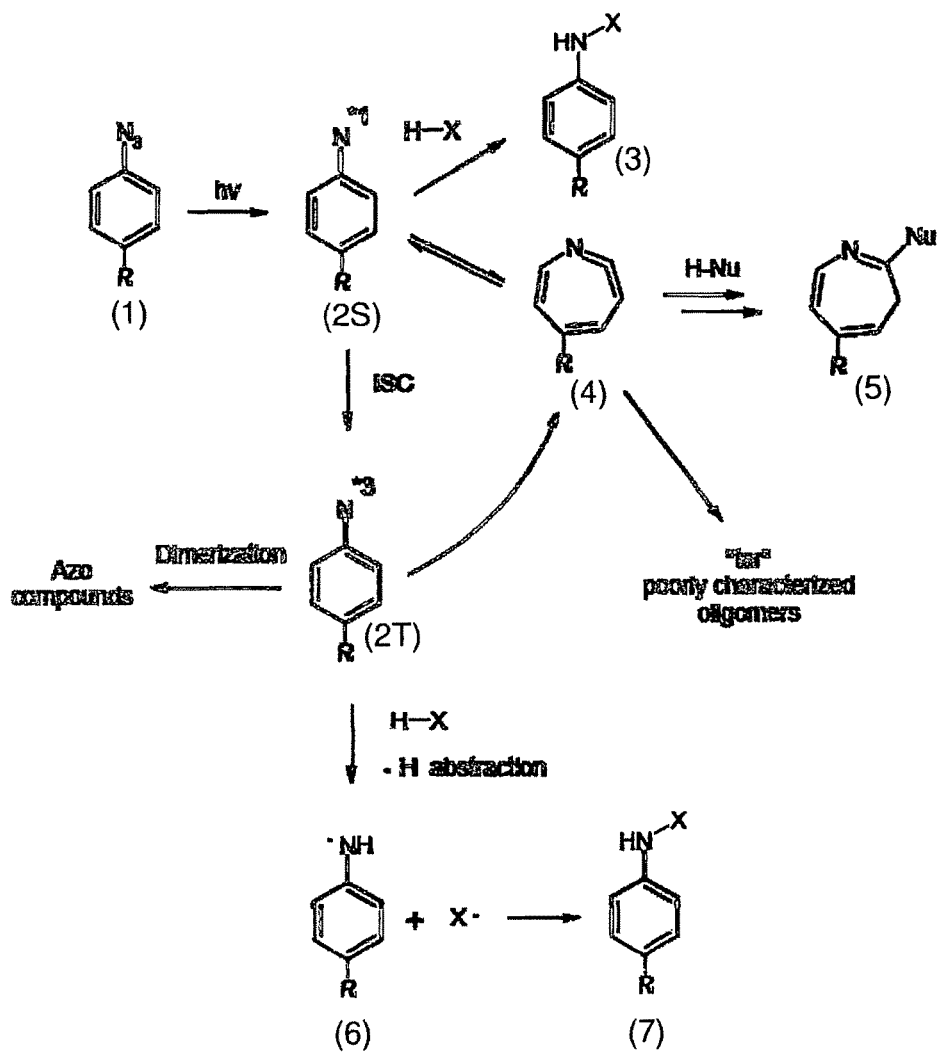
FIG. 9 shows the reaction mechanism for light excitation of arylazides of the invention.
Figure 10:
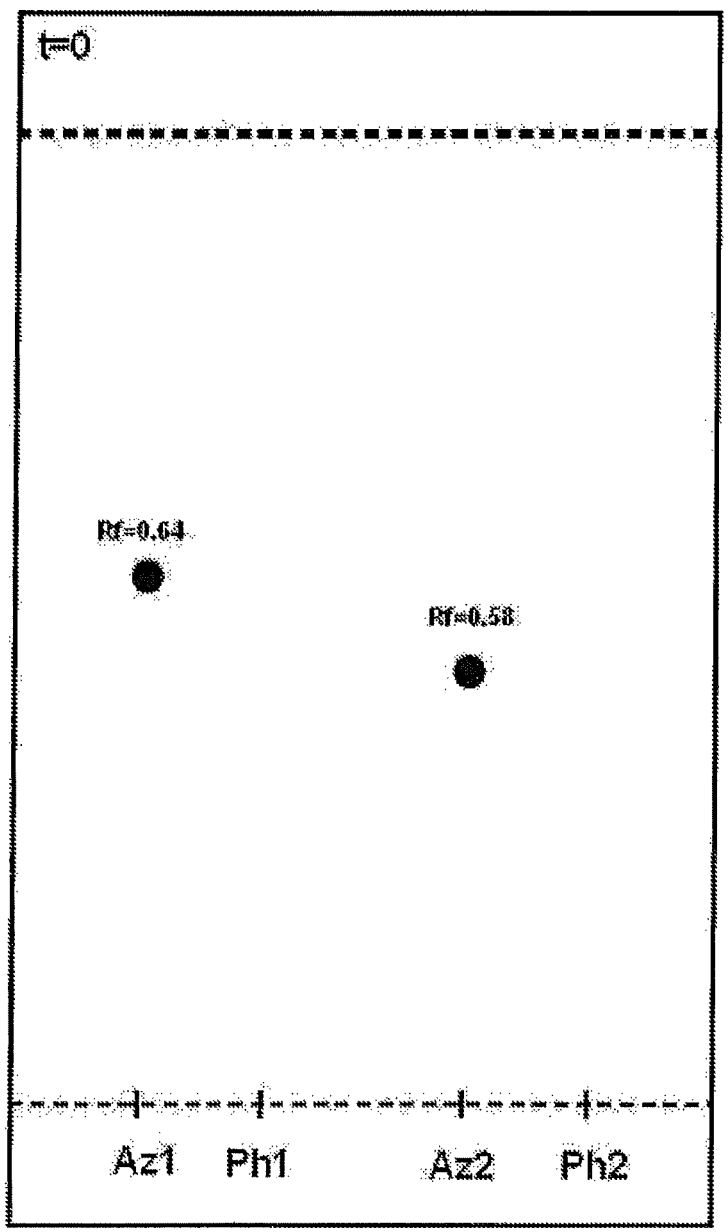
FIGS. 10-13 show the TLC obtained for the preparation of the compounds according to EXAMPLE 13.
Figure 11:
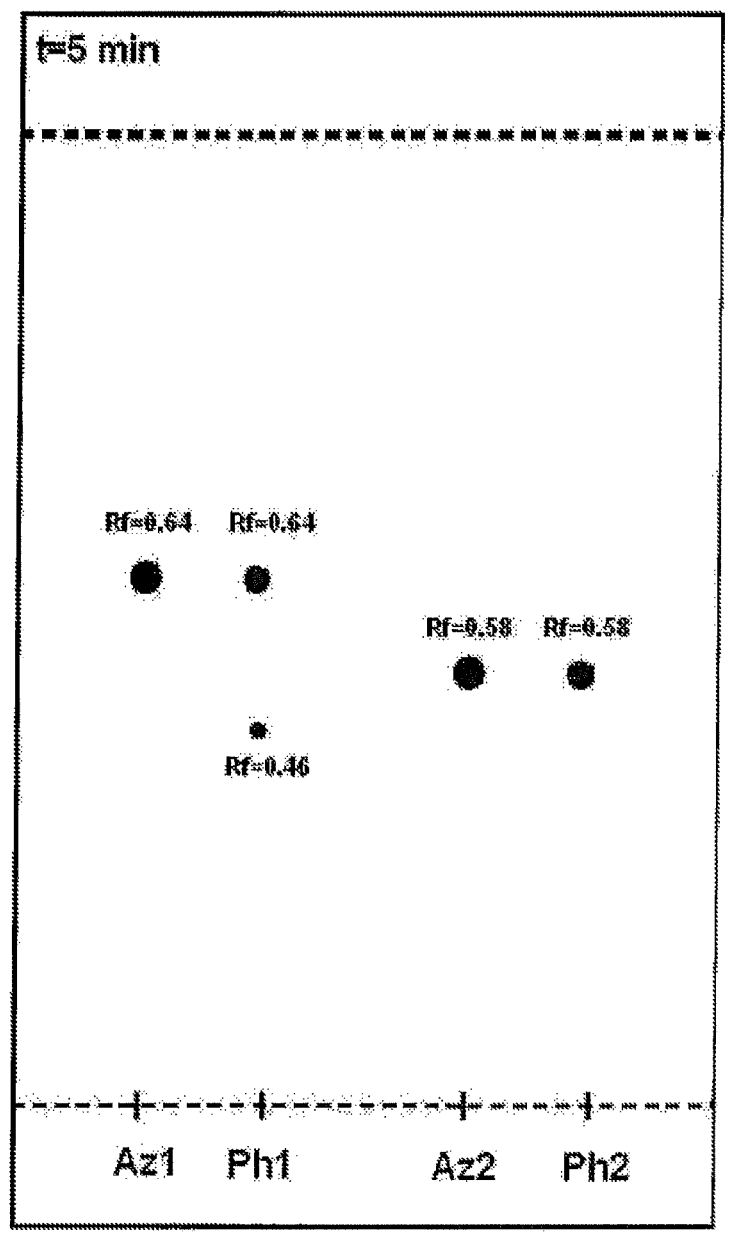
Figure 12:
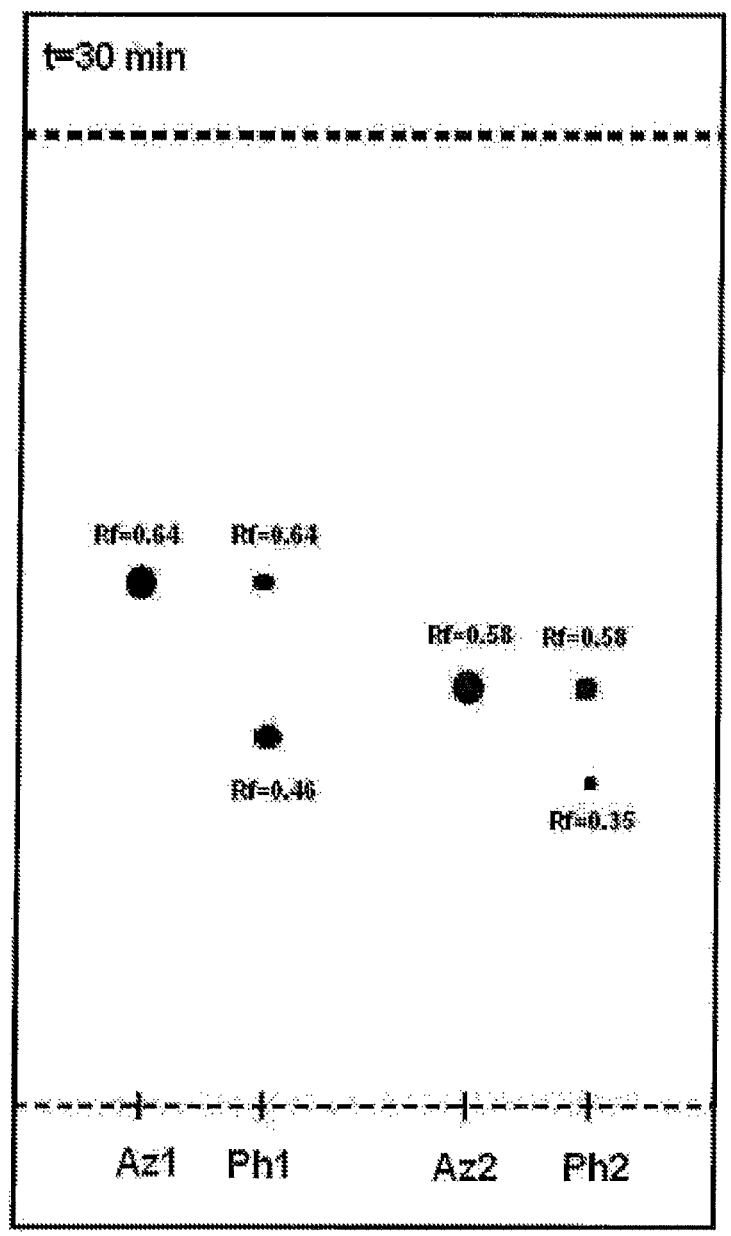
Figure 13:
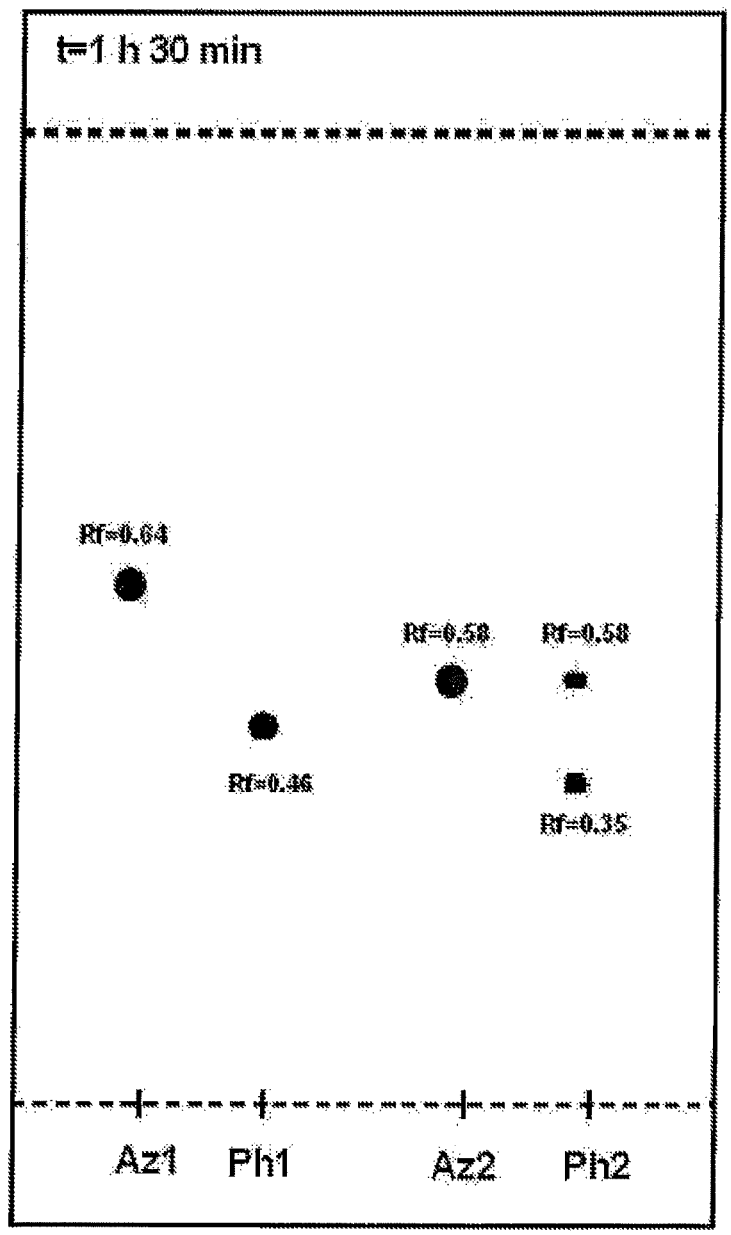

The proposed reaction mechanism for light excitation of arylazides is summarized in FIG. 9 ("Thrombin inhibitors grafting on polyester membranes for the preparation of blood-compatible materials", Claudio Salvagnini, 2005).

Firstly arylazide (1) undergoes loss of molecular nitrogen and transient formation of singlet arylnitrene (2S). This unstable compound may rapidly react by insertion on hydrocarbons (3) or by internal rearrangement to 1,2-azacycloheptatetraene (4). This is an electron-deficient species and it reacts predominantly with nucleophiles (Nu), forming azepine adducts (5). A small amount of triplet nitrene species (2T) is formed through a process of intersystem crossing. Triplet nitrene is essentially a diradical species that is capable of hydrogen-radical abstraction and covalent binding to hydrocarbon substrates (7).

For the treatment of the polymeric surface according to the invention, in order to enhance the hydrophilic or hydrophobic character of the polymeric material surface, and in particular for a good yield of the photoactivation reaction, it is important that most part of the arylazide in the solution reacts by covalent bindings to hydrocarbon substrates (3) or (7). In particular, for a good yield of the photoactivation reaction, it is important that only a residual part of the arylazide in the solution reacts by forming azepine adducts (5), which represents a waste of the reaction.

Coming back to the reaction, once formed the singlet arylnitrene (2S) usually undergoes intersystem crossing to the corresponding triplets at rates that depend on the nature of the nitrene. For covalent bond formation, singlet arylnitrene is better since it acquires an electron pair from its substrate in a single reaction step. The electronic nature of triplet nitrene (2T), on the contrary, forces it to undergo two-steps reactions in which a covalent bond between the nitrene and its substrate is often made only in the second step.

For this reason, usually in the reaction mechanism for light excitation of arylazides, the azepine formation is the major reaction path while only a small part of the singlet arylnitrene (2s) is slowly converted into hydrocarbon substrates (3) or into triplet nitrene (2T).

As anticipated above, for a good yield of the photoactivation reaction it is important that most part of the arylazide in the solution reacts by covalent bindings with hydrocarbon substrates (3) or (7). Compounds [4-azido-2,3,5,6-tetrafluoro-N-(3-hydroxypropyl)benzamide of Example 5; 4-azido-2,3,5,6-tetrafluoro-N-(4,4,5,5,6,6,7,7,8,8,9,9,10,10,11,11,11-heptadecafluoroundecyl)benzamide of Example 6; 2-nitro-5-azidobenzoylglycine of Example 7; N-(4,4,5,5,6,6,7,7,8,8,9,9,10,10,11,11,11-heptadecafluoroundecyl) 5-azido-2-nitrobenzoate of Example 8; N-(tris(hydroxymethyl)-5-azido-2-nitrobenzoate of Example 9 and N-(dodecaethylene glycol monomethyl ether)-5-azido-2-nitrobenzoate of Example 10 have shown to provide good reaction rate and yield.

The photoactivation reactions of these substituted aromatic azides have been studied by using UV irradiation light. Two different samples have been prepared with:
- 3 ml of a solution $10^{-2}$ M of N-(2-hydroxyethyl)-4-azidobenzenesulphonylamide of Example 3 (Az1);
- 3 ml of a solution $10^{-2}$ M of 4-azido-2,3,5,6-tetrafluoro-N-(3-hydroxypropyl)benzamide of Example 5 (Az2).

The solvent used for the samples was methanol. A PA12 surface has been immersed in each solution, and the samples have been irradiated with a light wavelength of 254 nm.

These samples were tested at different times with a TLC test (eluent: 100% of ethyl acetate) in order to evaluate the yield of the photoactivation reaction. The TLC results of the photoactivation reaction, provided at different times and for both the samples Az1 and Az2, are shown in FIGS. 10-13.

Time t=0

The presence of the azide is indicated by a spot and correlated to a specific distance Rf, where $$R_f = \frac{\text{distance travelled by the compound}}{\text{distance travelled by the solvent font}}$$

At the starting point, it is possible to see the presence of two spots which represent the two azides, and in particular the presence of arylazide available for the reaction with the polymeric surface. The specific starting values of $R_f$ are: $R_{fAz1}$=00.64 for AZ1 and $R_{fAz2}$=0.58 for AZ2.

Time t=5 minutes

After a certain reaction period (5 minutes) it is possible to detect also the spots corresponding to the products of the two reactions, indicated as Ph1 and Ph2 respectively.

In particular, as regards the reaction concerning the N-(2-hydroxyethyl)-4-azidobenzenesulphonylamide, it is possible to see:
- a very small spot (as compared to the spot of t=0) corresponding to a small amount of arylnitrene available for the reaction and indicated by the same $R_{fAz1}$=0.64;
- a new spot, corresponding to a small amount of azepine, indicated by $R_{fPh1}$=0.46. This situation indicates that part of arylnitrene has been transformed into azepine.

As regards the reaction concerning the 4-azido-2,3,5,6-tetrafluoro-N-(3-hydroxypropyl)benzamide, it is possible to see only a small spot (as compared to the spot of t=0) corresponding to a small amount of arylazide available for the reaction and indicated by the same $R_{fAz2}$=0.58. In this situation, the absence of azepine (i.e. the absence of the relative spot) and the decrease in the amount of arylazide available for the reaction (i.e. represented by a small relative spot) indicates that part of arylnitrene has reacted with the polymeric surface.

Time t=30 minutes

At this stage of the reaction, in considering the N-(2-hydroxyethyl)-4-azidobenzenesulphonylamide, it is still possible to see both of the spots: the spot corresponding to arylazide ($R_{fAz1}$=0.64) (which is further decreased) and the spot corresponding to azepine ($R_{fPh1}$=0.46) (which is increased).

As regards the reaction concerning the 4-azido-2,3,5,6-tetrafluoro-N-(3-hydroxypropyl)benzamide, it is now possible to see:
- the small spot corresponding to arylazide available for the reaction and indicated by the same $R_{fAz2}$=0.58;
- a new spot, corresponding to a small amount of azepine, indicated by $R_{fPh2}$=0.35. This situation indicates that only now part of arylnitrene has been transformed in azepine.

Time t=1 hour and 30 minutes

At this stage of the reaction, in considering the N-(2-hydroxyethyl)-4-azidobenzenesulphonylamide, it is possible to see only the spot corresponding to azepine ($R_{fPh1}$=0.46). This situation indicates that there is no more arylnitrene available for the reaction with the polymeric surface and thus the reaction is terminated.

As regards the reaction concerning the 4-azido-2,3,5,6-tetrafluoro-N-(3-hydroxypropyl)benzamide, it is still possible to see both of the spots: the small spot corresponding to arylazide available for the reaction and the spot corresponding to azepine. This situation indicates that there is still arylnitrene available for the reaction with the polymeric surface and thus the reaction is still on-going.

The TLC measures obtained for the azide with electron-withdrawing substituents shows that the azepine, which represents a reaction waste, does not appear immediately. The above results show that the azide enhanced with electron-withdrawing substituents (for example —F and —$NO_2$) have a good yield of the photoactivation reaction with the polymeric surface.

We claim:

1. A balloon catheter comprising a balloon made of a polymeric material, said balloon having a surface, characterised in that said surface comprises covalently bound groups of the following formula:

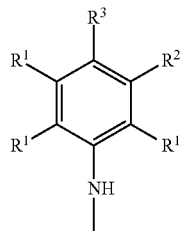

wherein:
each $R^1$ is independently H or F;
$R^2$ is a Z group selected from the group consisting of —C(O)NH—$R_a$, —S(O)$_2$NH—$R_a$, and —P(O)$_2$NH—$R_a$;
wherein $R_a$ is a $C_1$-$C_4$ linear or branched saturated alkyl chain optionally substituted with one or more polar functional groups, or with a —(CF$_2$)$_m$—CF$_3$ perfluoroalkyl group, wherein m is 1 to 70; or
wherein $R_a$ is —(CHRCH$_2$O)$_n$—X, wherein n is 1 to 70, R is H or —CH$_3$, and X is selected from the group consisting of H, a saturated branched or linear $C_1$-$C_4$ alkyl chain, and a —(CH$_2$)$_p$—O—(CH$_2$)$_q$—W group, wherein W is H, —CH$_3$, or —NH$_2$, and wherein p and q are independently 1 to 30; or
wherein $R_a$ is a $C_1$-$C_{70}$ linear or branched saturated alkyl chain or an aromatic compound; and
$R^3$ is —$NO_2$.

2. The balloon catheter according to claim 1, wherein the linear or branched saturated alkyl chain within $R_a$ is selected from the group consisting of hydrocarbon chains, polyethylene, polypropylene, and polyolefins.

3. The balloon catheter according to claim 1, wherein the aromatic group of $R_a$ is selected from the group consisting of xylene, polystyrene, and acrylonitrile butadiene styrene.

4. The balloon catheter according to claim 1, wherein within the Z group, $R_a$ is selected from the group consisting of —(CH$_2$CH$_2$)OH, —(CH$_2$CH$_2$CH$_2$)OH, —C(CH$_2$OH)$_3$, —(CH(CH$_3$)CH$_2$O)$_9$—CH$_2$CH$_2$OCH$_3$, and —(CH$_2$)(CF$_2$)$_7$CF$_3$.

5. The balloon catheter according to claim 1, wherein the polymeric material comprises a polyimide-based copolymer of general formula H—(O-PF-OOC-PA-COO-PF-OOC-PA-CO)$_n$—OH wherein:
PA is a polyamide segment;
PF is a diol segment comprising OH-terminating dimer diol polyesters; and
n is between 5 and 20;

or wherein the polymeric material comprises an elastomer obtained by the polymerization of a polyamide forming block compound selected from the group consisting of an aminocarboxylic acid of formula (1) below and a lactam of formula (2) below:

$$H_2N—R^1—COOH \qquad (1)$$

with a polyetherdiaminic triblock of formula (3) below:

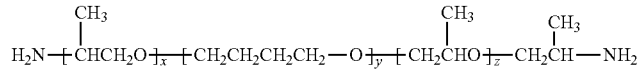

and a dicarboxylic acid of formula (4) below:

$$HOOC—(R^3)_m—COOH \qquad (4)$$

wherein $R^1$, $R^2$, and $R^3$ are each binding groups comprising a hydrocarbon chain therein, which may be interrupted by one or more amide groups; and
wherein x ranges from 1 to 20, y ranges from 4 to 50, z ranges from 1 to 20, and wherein m is 0 or 1.

6. The balloon catheter according to claim 1, wherein said surface comprises hydrophilic groups.

7. The balloon catheter according to claim 1, wherein said surface comprises hydrophobic groups.

8. The balloon catheter according to claim 1, wherein said surface is the outer surface of the balloon.

9. The balloon catheter according to claim 1, wherein said surface is the inner surface of the balloon.

10. The balloon catheter according to claim 1, wherein said surface is the inner and the outer surface of the balloon.

11. The balloon catheter according to claim 1, wherein said surface is the outer surface of the balloon and at least one active substance is bound to at least one portion of said outer surface.

12. The balloon catheter according to claim 11, wherein the active substance is directly bound to the balloon outer surface.

13. The balloon catheter according to claim 11, wherein the active substance is bound to the balloon outer surface by means of a bridge substance that is suitable for linking or encapsulating the active substance.

14. A method for modifying the balloon surface of the balloon catheter of claim 1, said method comprising the steps of:
a) preparing a solution of a compound of the following formula:

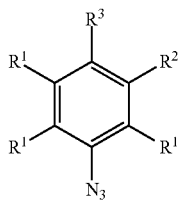

wherein:

each $R^1$ is independently H or F;

$R^2$ is a Z group selected from the group consisting of —C(O)NH—$R_a$, —S(O)$_2$NH—$R_a$, and —P(O)$_2$NH—$R_a$;

wherein $R_a$ is a $C_1$-$C_4$ linear or branched saturated alkyl chain optionally substituted with one or more polar functional groups, or with a —(CF$_2$)$_m$—CF$_3$ perfluoroalkyl group, wherein m is 1 to 70; or wherein $R_a$ is —(CHRCH$_2$O)$_n$—X, wherein n is 1 to 70, R is H or —CH$_3$, and X is selected from the group consisting of H, a saturated branched or linear $C_1$-$C_4$ alkyl chain, and a —(CH$_2$)$_p$—O—(CH$_2$)$_q$—W group, wherein W is H, —CH$_3$, or —NH$_2$, and wherein p and q are independently 1 to 30; or wherein $R_a$ is a $C_1$-$C_{70}$ linear or branched saturated alkyl chain or an aromatic compound; and $R^3$ is —NO$_2$;

b) contacting the balloon surface with the solution prepared from step a);

c) irradiating the balloon surface obtained from step b) with a radiation capable of photoactivating said surface.

15. The method according to claim 14, wherein the compound of formula (I) is selected in the group consisting of: 2-nitro-5-azidobenzoylglycine, N-(4,4,5,5,6,6,7,7,8,8,9,9,10,10,11,11,11-heptadeca fluoroundecyl)5-azido-2-nitrobenzoate, N-(tris(hydroxymethyl)-5-azido-2-nitrobenzoate, N-(dodecaethylene glycol monomethyl ether)-5-azido-2-nitrobenzoate, and N-(Hexadecyl)-5-azido-2-nitrobenzoate.

16. The method according to claim 14, wherein the solvent of step a) is selected from methanol, ethanol, acetonitrile and chloroform.

17. The method according to claim 14, wherein said radiation has a wavelength capable of passing through the polymeric material of the balloon catheter.

18. The method according to claim 14, wherein said radiation has a wavelength comprising from about 200 nm to about 600 nm.

19. The method according to claim 14, wherein the irradiation of step c) is performed in a dark environment at room temperature.

20. The method according to claim 14, wherein the irradiation of step c) is performed for about 0.5-1 hour.

21. The method according to claim 14, wherein step b) is performed by flowing the solution comprising the compound of formula (I) through the balloon surface.

22. The method according to claim 14, comprising, before step b), a step wherein the balloon surface to be treated is washed and dried.

23. The method according to claim 14, wherein after step b), the balloon surface is washed in order to remove the unbound compounds of formula (I).

24. The method according to claim 14, wherein the balloon surface is the balloon inner surface, the balloon outer surface or both.

25. The balloon catheter according to claim 1, wherein $R_a$ is a $C_1$-$C_4$ linear or branched saturated alkyl chain substituted with one or more polar functional groups, or with a —(CF$_2$)$_m$—CF$_3$ perfluoroalkyl group, wherein m is 1 to 70.

26. The balloon catheter according to claim 25, wherein the polar functional groups are selected from the group consisting of —OH, —COOH, —SO$_3$, —PO$_4$, —NH$_2$, and —NH$_4^+$.

27. The balloon catheter according to claim 5, wherein $R^1$ and $R^2$ independently represent an alkylene group having 2 to 20 carbon atoms and amide bonds, and $R^3$ is an alkylene group having 1 to 20 carbon atoms.

* * * * *